United States Patent
Schulte et al.

(10) Patent No.: US 9,884,206 B2
(45) Date of Patent: Feb. 6, 2018

(54) SYSTEMS AND METHODS FOR INTENSITY MODULATED RADIATION THERAPY

(71) Applicants: Loma Linda University, Loma Linda, CA (US); Yair Censor, Loma Linda, CA (US)

(72) Inventors: Reinhard W. Schulte, Grand Terrace, CA (US); Yair Censor, Nave-Shaanan (IL)

(73) Assignees: Loma Linda University Medical Center, Loma Linda, CA (US); Carmel-HAIFA University Economic Corporation Ltd., Haifa (IL)

( * ) Notice: Subject to any disclaimer, the term of this patent is extended or adjusted under 35 U.S.C. 154(b) by 7 days.

(21) Appl. No.: 15/217,946

(22) Filed: Jul. 22, 2016

(65) Prior Publication Data

US 2017/0028220 A1 Feb. 2, 2017

Related U.S. Application Data

(60) Provisional application No. 62/196,273, filed on Jul. 23, 2015.

(51) Int. Cl.
*G06K 9/00* (2006.01)
*A61N 5/10* (2006.01)

(52) U.S. Cl.
CPC ........... *A61N 5/1042* (2013.01); *A61N 5/103* (2013.01); *A61N 5/1084* (2013.01); *A61N 2005/1087* (2013.01); *A61N 2005/1089* (2013.01)

(58) Field of Classification Search
USPC ......... 250/306, 307, 309, 310, 492.1, 492.2, 250/492.21, 492.3, 396 R, 505.1; 378/65
See application file for complete search history.

(56) References Cited

U.S. PATENT DOCUMENTS

| | | |
|---|---|---|
| 3,777,124 A | 12/1973 | Pavkovich |
| 3,783,251 A | 1/1974 | Pavkovich |

(Continued)

FOREIGN PATENT DOCUMENTS

| | | |
|---|---|---|
| DE | 3 643 893 | 6/1988 |
| DE | 10 2005 034 912 | 2/2007 |

(Continued)

OTHER PUBLICATIONS

Brahme, et al.: "Optimization of Proton and Heavy Ion Therapy Using an Adaptive Inversion Algorithm", Radiotherapy and Oncology, vol. 15, Jun. 1989, pp. 189-197.

(Continued)

*Primary Examiner* — Bernard Souw
(74) *Attorney, Agent, or Firm* — Knobbe Martens Olson & Bear LLP

(57) ABSTRACT

Embodiments disclosed herein include methods for performing intensity-modulated radiation therapy on a subject using a plurality of pencil beams. The methods can include generating a treatment plan for intensity-modulated radiation therapy that satisfies dose constraints for each of a plurality of sub-volumes. The treatment plan can be generated using a superiorization technique that reduces total variation in dose space. Additional dose-volume constraints that permit a fraction of treatment doses to violate a prescription by up to a defined percentage of intensity can be used to assist in determining the treatment plan.

35 Claims, 20 Drawing Sheets

(56) References Cited

U.S. PATENT DOCUMENTS

| | | |
|---|---|---|
| 3,852,610 A | 12/1974 | McIntyre |
| 3,942,012 A | 3/1976 | Boux |
| 3,955,089 A | 5/1976 | McIntyre et al. |
| 3,975,640 A | 8/1976 | Boux et al. |
| 3,986,026 A | 10/1976 | Martin |
| 4,020,356 A | 4/1977 | Brahme |
| 4,069,457 A | 1/1978 | Martin et al. |
| 4,095,114 A | 6/1978 | Taumann |
| 4,112,306 A | 9/1978 | Nunan |
| 4,230,129 A | 10/1980 | LeVeen |
| 4,378,813 A | 4/1983 | Lovelace et al. |
| 4,442,352 A | 4/1984 | Brahme |
| 4,705,955 A | 11/1987 | Mileikowsky |
| 4,726,046 A | 2/1988 | Nunan |
| 4,827,491 A | 5/1989 | Barish |
| 4,831,254 A | 5/1989 | Jenkins |
| 4,845,370 A | 7/1989 | Thompson et al. |
| 4,868,843 A | 9/1989 | Nunan |
| 4,870,287 A | 9/1989 | Cole et al. |
| 5,017,789 A | 5/1991 | Young et al. |
| 5,027,818 A | 7/1991 | Bova et al. |
| 5,037,374 A | 8/1991 | Carol |
| 5,039,861 A | 8/1991 | Swenson |
| 5,039,867 A | 8/1991 | Nishihara et al. |
| 5,107,839 A | 4/1992 | Houdek et al. |
| 5,115,391 A | 5/1992 | Puthenpura et al. |
| 5,117,829 A | 6/1992 | Miller et al. |
| 5,206,893 A | 4/1993 | Hara |
| 5,242,455 A | 9/1993 | Skeens et al. |
| 5,278,886 A | 1/1994 | Kobiki et al. |
| 5,297,037 A | 3/1994 | Ifuku |
| 5,317,164 A | 5/1994 | Kurokawa |
| 5,343,048 A | 8/1994 | Pastyr |
| 5,427,097 A | 6/1995 | Depp |
| 5,440,133 A | 8/1995 | Moyers et al. |
| 5,446,548 A | 8/1995 | Gerig et al. |
| 5,511,549 A | 4/1996 | Legg et al. |
| 5,547,454 A | 8/1996 | Horn et al. |
| 5,585,642 A | 12/1996 | Britton et al. |
| 5,596,199 A | 1/1997 | McNulty et al. |
| 5,596,619 A | 1/1997 | Carol |
| 5,602,892 A | 2/1997 | Llacer |
| 5,668,371 A | 9/1997 | Deasy et al. |
| 5,745,545 A | 4/1998 | Hughes |
| 5,751,781 A | 5/1998 | Brown et al. |
| 5,754,623 A | 5/1998 | Seki |
| 5,760,395 A | 6/1998 | Johnstone |
| 5,769,779 A | 6/1998 | Alderson |
| 5,820,553 A | 10/1998 | Hughes |
| 5,847,403 A | 12/1998 | Hughes et al. |
| 5,851,182 A | 12/1998 | Sahadevan |
| 5,866,912 A | 2/1999 | Slater et al. |
| 6,052,435 A | 4/2000 | Hernandez-Guerra et al. |
| 6,104,779 A | 8/2000 | Shepherd et al. |
| 6,144,875 A | 11/2000 | Schweikard et al. |
| 6,148,272 A | 11/2000 | Bergstrom et al. |
| 6,200,025 B1 | 3/2001 | Rich |
| 6,240,161 B1 | 5/2001 | Siochi |
| 6,275,564 B1 | 8/2001 | Ein-Gal |
| 6,316,776 B1 | 11/2001 | Hiramoto et al. |
| 6,345,114 B1 | 2/2002 | Mackie et al. |
| 6,385,286 B1 | 5/2002 | Fitchard et al. |
| 6,437,513 B1 | 8/2002 | Selzer et al. |
| 6,473,490 B1 | 10/2002 | Siochi |
| 6,577,707 B2 | 6/2003 | Siochi |
| 6,736,831 B1 | 5/2004 | Hartmann et al. |
| 6,757,355 B1 | 6/2004 | Siochi |
| 6,774,383 B2 | 8/2004 | Norimine et al. |
| 6,777,700 B2 | 8/2004 | Yanagisawa et al. |
| 6,795,523 B2 | 9/2004 | Steinberg |
| 6,804,548 B2 | 10/2004 | Takahashi et al. |
| 6,809,325 B2 | 10/2004 | Dahl et al. |
| 6,810,107 B2 | 10/2004 | Steinberg |
| 6,814,694 B1 | 11/2004 | Pedroni |
| 6,822,244 B2 | 11/2004 | Beloussov et al. |
| 6,953,943 B2 | 10/2005 | Yanagisawa et al. |
| 6,977,987 B2 | 12/2005 | Yamashita et al. |
| 7,084,410 B2 | 8/2006 | Beloussov et al. |
| 7,085,347 B2 | 8/2006 | Mihara et al. |
| 7,193,227 B2 | 3/2007 | Hiramoto et al. |
| 7,194,063 B2 | 3/2007 | Dilmanian et al. |
| 7,268,358 B2 | 9/2007 | Ma et al. |
| 7,317,192 B2 | 1/2008 | Ma |
| 7,368,740 B2 | 5/2008 | Beloussov et al. |
| 7,398,309 B2 | 7/2008 | Baumann et al. |
| 7,560,715 B2 | 7/2009 | Pedroni |
| 7,629,598 B2 | 12/2009 | Harada |
| 7,692,168 B2 | 4/2010 | Moriyama et al. |
| 7,755,068 B2 | 7/2010 | Ma et al. |
| 7,791,051 B2 | 9/2010 | Beloussov et al. |
| 7,801,270 B2 | 9/2010 | Nord et al. |
| 7,801,988 B2 | 9/2010 | Baumann et al. |
| 7,807,987 B2 | 10/2010 | Braess |
| 7,820,989 B2 | 10/2010 | Sommer |
| 7,825,388 B2 | 11/2010 | Nihongi et al. |
| 7,834,334 B2 | 11/2010 | Grozinger et al. |
| 7,838,855 B2 | 11/2010 | Fujii |
| 7,903,781 B2 | 3/2011 | Foland et al. |
| 7,920,675 B2 | 4/2011 | Lomax et al. |
| 8,080,801 B2 | 12/2011 | Safai |
| 8,085,899 B2 | 12/2011 | Nord et al. |
| 8,109,865 B2 | 2/2012 | Jackson |
| 8,129,699 B2 | 3/2012 | Balakin |
| 8,129,701 B2 | 3/2012 | Al-Sadah et al. |
| 8,154,001 B2 | 4/2012 | Flynn et al. |
| 8,175,892 B2 | 5/2012 | Kapoor et al. |
| 8,217,373 B2 | 7/2012 | Bert et al. |
| 8,253,121 B2 | 8/2012 | Gnutzmann et al. |
| 8,264,174 B2 | 9/2012 | Liu et al. |
| 8,299,448 B2 | 10/2012 | Bert et al. |
| 8,309,939 B2 | 11/2012 | Harada et al. |
| 8,354,656 B2 | 1/2013 | Beloussov et al. |
| 8,395,131 B2 | 3/2013 | Wu et al. |
| 8,461,559 B2 | 6/2013 | Lomax |
| 8,598,546 B2 | 12/2013 | Bert et al. |
| 8,601,116 B2 | 12/2013 | Baumann et al. |
| 8,644,571 B1 * | 2/2014 | Schulte ............... A61N 5/1039 250/307 |
| 8,737,707 B2 | 5/2014 | Pearlstein et al. |
| 9,220,920 B2 | 12/2015 | Schulte et al. |
| 9,289,627 B2 | 3/2016 | Otto |
| 2002/0051513 A1 | 5/2002 | Pugachev et al. |
| 2002/0077545 A1 | 6/2002 | Takahashi et al. |
| 2003/0086527 A1 | 5/2003 | Speiser et al. |
| 2003/0155530 A1 | 8/2003 | Adnani et al. |
| 2004/0034438 A1 | 2/2004 | Uematsu |
| 2004/0098445 A1 | 5/2004 | Baumann et al. |
| 2005/0072940 A1 | 4/2005 | Beloussov et al. |
| 2006/0145088 A1 | 7/2006 | Ma |
| 2006/0166353 A1 | 7/2006 | Alfano et al. |
| 2007/0018121 A1 | 1/2007 | Leyman et al. |
| 2007/0034812 A1 | 2/2007 | Ma et al. |
| 2007/0225603 A1 | 9/2007 | Jackson |
| 2008/0067401 A1 | 3/2008 | Harada |
| 2008/0164416 A1 | 7/2008 | Safai |
| 2008/0192892 A1 | 8/2008 | Dilmanian et al. |
| 2008/0237494 A1 | 10/2008 | Beloussov et al. |
| 2008/0237495 A1 | 10/2008 | Grozinger et al. |
| 2008/0260098 A1 | 10/2008 | Al-Sadah et al. |
| 2009/0039256 A1 | 2/2009 | Fujii et al. |
| 2009/0154644 A1 | 6/2009 | Nord et al. |
| 2009/0168960 A1 | 7/2009 | Jongen et al. |
| 2009/0189095 A1 | 7/2009 | Flynn et al. |
| 2009/0212231 A1 | 8/2009 | Hill et al. |
| 2009/0261275 A1 | 10/2009 | Rietzel |
| 2009/0304154 A1 | 12/2009 | Lomax et al. |
| 2009/0309046 A1 | 12/2009 | Balakin |
| 2010/0074408 A1 | 3/2010 | Bert et al. |
| 2010/0088339 A1 | 4/2010 | Rietzel et al. |
| 2010/0108903 A1 | 5/2010 | Bert et al. |
| 2010/0171047 A1 | 7/2010 | Matsuda |
| 2010/0171447 A1 | 7/2010 | Balakin |
| 2010/0187446 A1 | 7/2010 | Dilmaniam et al. |
| 2010/0213394 A1 | 8/2010 | Fieres |

(56) References Cited

U.S. PATENT DOCUMENTS

| | | | |
|---|---|---|---|
| 2010/0288946 | A1 | 11/2010 | Honda et al. |
| 2010/0301235 | A1 | 12/2010 | Bert et al. |
| 2011/0101236 | A1 | 5/2011 | Cameron et al. |
| 2011/0118531 | A1 | 5/2011 | Balakin |
| 2011/0180731 | A1 | 7/2011 | Welsh |
| 2011/0233423 | A1 | 9/2011 | Balakin |
| 2011/0238440 | A1 | 9/2011 | Leuschner |
| 2011/0297850 | A1 | 12/2011 | Claereboudt et al. |
| 2011/0309255 | A1 | 12/2011 | Bert et al. |
| 2012/0025076 | A1* | 2/2012 | Kraft ............... A61N 5/1049 250/307 |
| 2012/0056109 | A1 | 3/2012 | Lomax |
| 2012/0136194 | A1 | 5/2012 | Zhang et al. |
| 2012/0205557 | A1 | 8/2012 | Rinecker |
| 2012/0224667 | A1 | 9/2012 | Cheng et al. |
| 2013/0090549 | A1 | 4/2013 | Meltsner et al. |
| 2013/0345489 | A1 | 12/2013 | Beloussov |

FOREIGN PATENT DOCUMENTS

| | | |
|---|---|---|
| DE | 10 2007 032 025 | 12/2008 |
| EP | 0 237 165 | 9/1987 |
| EP | 0 247 449 | 12/1987 |
| EP | 0 586 152 | 3/1994 |
| EP | 1 584 353 | 10/2005 |
| EP | 1 900 392 | 3/2008 |
| EP | 2 030 650 | 3/2009 |
| EP | 2 116 277 | 11/2009 |
| EP | 2 392 383 | 12/2011 |
| EP | 2 420 288 | 2/2012 |
| JP | H01-209077 | 8/1989 |
| WO | WO 95/001207 | 1/1995 |
| WO | WO 96/025200 | 8/1996 |
| WO | WO 00/016342 | 3/2000 |
| WO | WO 01/000276 | 1/2001 |
| WO | WO 04/109717 | 12/2004 |
| WO | WO 05/057738 | 6/2005 |
| WO | WO 05/102453 | 11/2005 |
| WO | WO 06/060886 | 6/2006 |
| WO | WO 06/094533 | 9/2006 |
| WO | WO 07/012646 | 2/2007 |
| WO | WO 08/003526 | 1/2008 |
| WO | WO 08/003527 | 1/2008 |
| WO | WO 08/106483 | 9/2008 |
| WO | WO 08/106496 | 9/2008 |
| WO | WO 09/135879 | 11/2009 |
| WO | WO 09/142546 | 11/2009 |
| WO | WO 10/043340 | 4/2010 |
| WO | WO 10/049071 | 5/2010 |
| WO | WO 10/101489 | 9/2010 |
| WO | WO 10/105858 | 9/2010 |
| WO | WO 10/149740 | 12/2010 |
| WO | WO 11/091104 | 7/2011 |
| WO | WO 11/126805 | 10/2011 |
| WO | WO 11/139863 | 11/2011 |
| WO | WO 11/154853 | 12/2011 |
| WO | WO 11/162851 | 12/2011 |
| WO | WO 12/024448 | 2/2012 |

OTHER PUBLICATIONS

Coutrakon, G. et al., "A Prototype Beam Delivery System for the Proton Medical Accelerator at Loma Linda", Medical Physics, vol. 18, No. 6, Nov./Dec. 1991.

Cuperus et al.: "Automatic Generation of Configuration Files for a Distributed Control System," Proceedings of the 1995 International Conference on Accelerator and Large Experimental Physics Control Systems (ICALEPCS1995), Chicago, IL, Oct. 30-Nov. 3, 1995, McC. Crowley-Milling (ed.), P. Lucas (ed.), P. Schoessow (ed.)., Fermi Lab-Co NF-96-069, 1996. S. 148-153.

Fermi National Accelerator Laboratory, "Design of a Proton Therapy Synchrotron" Jun. 1986, LL467-LL574.

Gottschalk, "Proton Radiotherapy Nozzle with Combined Scatterer/Modulator", dated Oct. 1987.

Kalet et al., "Designing radiotherapy software components and systems that will work together," Seminars in Radiation Oncology, Saunders, Philadelphia, PA, US, vol. 7, No. 1, Jan. 1997, pp. 11-20, XP005440845 ISSN: 1053-4296.

Katehakis et al.: "A Distributed, Agent-Based Architecture for the Acquisition, Management, Archiving and Display of Real-Time Monitoring Data in the Intensive Care Unit," Foundation for Research and Technology, Hellas, Institute of Computer Science, Technical Report [Online] No. 261, Oct. 1999 (Oct. 1999) URL:http://www.icsJorth.arifkatehaki/oublications/tr261.odf>.

Koehler, et al.: "Flattening of Proton Dose Distributions or Large-Field Radiotherapy", Medical Physics, vol. 4, No. 4, Jul./Aug. 1977, pp. 297-301.

Krause, et al.: "Re-Engineering of the GSI Control System," Proceedings of the 8th International Conference on Accelerator and Large Experimental Physics Control Systems (ICALEPCS2001), H. Shoace (ed.) San Jose, California, Nov. 27-30, 2001, eConfC011127, WEAT002. S. 219-221.

Marbach, et al.: "Optimization of Field Flatness and Depth-Dose for Therapy Electron Beams", Phys. Med. Biol, vol. 26, No. 3, 1981, pp. 435-443.

Metcalfe et al., "Patient Immobilization and Image Guidance," The Physics of Radiotherapy X-Rays and Electrons, Chapter 12: Jul. 15, 2007, p. 727-764.

Notice of Allowance dated Mar. 22, 2006 for U.S. Appl. No. 10/994,91.

Office Action dated Aug. 30, 2005 for U.S. Appl. No. 10/994,911.

Pyarali et al.: "Design and Performance of an Object-Oriented Framework for High-Speed Electronic Medical Imaging," Computing Systems, Usenix Association, Berkeley, CA US, vol. 9, No. 4, Jun. 1996, pp. 331-375.

Slater, James M. et al., "The Proton Treatment Center at Loma Linda University Medical Center: Rationale for and Description of its Development", I.J. Radiation Oncology Biol. Phys. vol. 22, pp. 383-389, 1992.

Weigel, et al., "Design and preparation of polymeric scaffolds for tissue engineering", Expert Rev Med Devices, 2006, vol. 3, Issue 6, pp. 835-851.

Yang, et al., "The design of scaffolds for use in tissue engineering. Part II. Rapid Prototyping techniques", Tissue Eng, 2002, vol. 8, Issue 1, pp. 1-11.

Archambeau et al., "Conceptual Design of a Proton Therapy Synchrotron for Loma Linda University Medical Center," Fermi National Accelerator Laboratory, Jun. 1986, in 106 pages.

Archambeau et al., "Design of a Proton Therapy Synchrotron," Fermi National Accelerator Laboratory, Jun. 1986, pp. LL467-LL574 in 54 pages.

Cole et al., "Proceedings of a Medical Workshop on Accelerators for Charged-Particle Beam Therapy" by Fermilab, Jan. 24-25, 1985, LL33170-LL33313 in 144 pages.

Flynn et al., "Comparison of intensity modulated x-ray therapy and intensity modulated proton therapy for selective subvolume boosting: a phantom study," Phys. Med. Biol., vol. 52, Oct. 21, 2007, pp. 6073-6091.

Krause, et al., "Adaption of a Synchrotron Control System for Heavy Ion Tumor Therapy," Proceedings of the 1995 International Conference on Accelerator and Large Experimental Physics Control Systems (ICALEPCS1995), Chicago, IL, Oct. 30-Nov. 3, 1995, McC. Crowley-Milling (ed.), P. Lucas (ed.), P. Schoessow (ed.)., Fermi Lab-Co NF-96-069, 1996. S. 14-19.

Laloup, J., "Cancer Therapy Without Side Effects Nearing Trials," dated Apr. 13, 2008 as copied from http://www.wired.com/print/medtech/health/news/2008/04/kanzius therapy on Apr. 23, 2008.

Paganetti, et al., "Proton Beam Radiotherapy—The State of the Art," AAPM 47th Annual Meeting, Seattle, WA, Jul. 25, 2005, in 36 pages.

Product Overview by BrainLAB Radiotherapy Solutions, 2004, BrainLAB AG, in 6 pages.

Proton Therapy Facility: Engineering Design Report, by Fermi National Accelerator Laboratory, Feb. 1987, LL45441-LL45570, in 130 pages.

(56) References Cited

OTHER PUBLICATIONS

Sadrozinski et al., Issues in Proton Computed Tomography, Nuclear Instruments and Methods in Physics Research A 511, Jun. 2003, pp. 275-281, in 7 pages.
Schulte et al., Nanoparticle-Enhanced Proton Computed Tomography: A Monte Carlo Simulation Study, Biomedical Imaging: Nano to Macro, 2004, IEEE International Symposium, Apr. 15-18, 2004, pp. 1354-1356 in 3 pages.

* cited by examiner

SYSTEMS AND METHODS FOR INTENSITY MODULATED RADIATION THERAPY

INCORPORATION BY REFERENCE TO ANY PRIORITY APPLICATIONS

Any and all applications for which a foreign or domestic priority claim is identified in the Application Data Sheet as filed with the present application, including U.S. Provisional Application No. 62/196,273, are hereby incorporated by reference under 37 CFR 1.57 and made a part of this specification.

BACKGROUND

Field

The present disclosure relates to radiation therapy systems and methods.

Description of the Related Art

Intensity-modulated radiation therapy (IMRT) includes intensity-modulated particle therapy (IMPT) using, for example, ions and intensity-modulated electromagnetic radiation therapy using, for example, x-rays for therapy applied to a subject. IMRT can be an effective means for providing conforming doses based on the specifications set by a planner or caregiver. Examples of IMPT treatment planning are disclosed in U.S. patent application Ser. No. 13/705,903, filed on Dec. 5, 2012, the entire contents of which are incorporated by reference and made a part of this specification. One strength of IMPT is that it allows for highly conforming doses to be given in a three-dimensional (3D) distribution target volumes while sparing an organ at risk (OAR).

As disclosed herein, the radiation in IMRT may refer to therapies using electromagnetic (e.g., photon) energy or particle energy. In some embodiments, IMRT can be adapted to use mathematical algorithms employed in inverse planning techniques.

It may be desirable for an IMRT therapist to define dosage bounds (e.g., upper limits and/or lower limits). Some embodiments can employ a process of multi-criteria optimization (MCO) in order to employ inverse planning techniques. Optimal solutions (e.g., Pareto-optimal solutions) can be achieved in various embodiments by a treatment planner or physician using MCO techniques.

SUMMARY

Example embodiments described herein have innovative features, no single one of which is indispensable or solely responsible for their desirable attributes. Without limiting the scope of the claims, some of the advantageous features will now be summarized.

Embodiments disclosed herein include methods for performing intensity-modulated radiation therapy on a subject using a plurality of pencil beams. The methods can include generating a treatment plan for intensity-modulated radiation therapy that satisfies dose constraints for each of a plurality of sub-volumes. The treatment plan can be generated using a superiorization technique that reduces total variation in dose space. Example superiorization techniques are disclosed in U.S. patent application Ser. No. 13/026,051, filed Feb. 11, 2011, the entire contents of which are incorporated by reference herein and made a part of this specification. Additional dose-volume constraints that permit a fraction of treatment doses to violate a prescription by up to a defined percentage of intensity can be used to assist in determining the treatment plan.

DETAILED DESCRIPTION OF SOME EMBODIMENTS

Figure 1A:
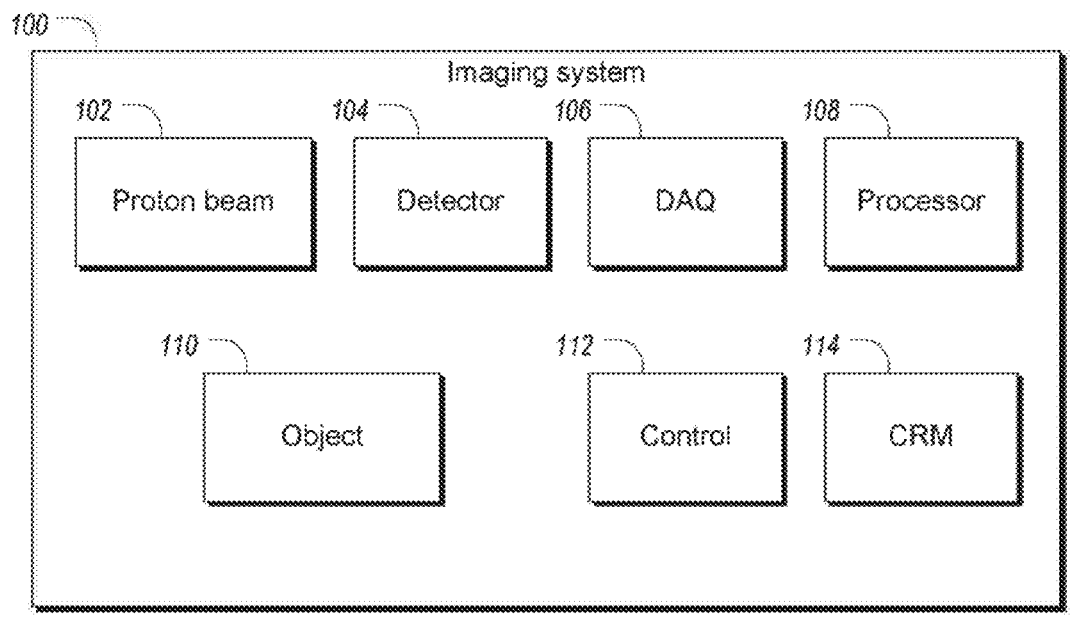
FIGS. 1A-1B schematically shows IMPT systems.
Figure 1B:
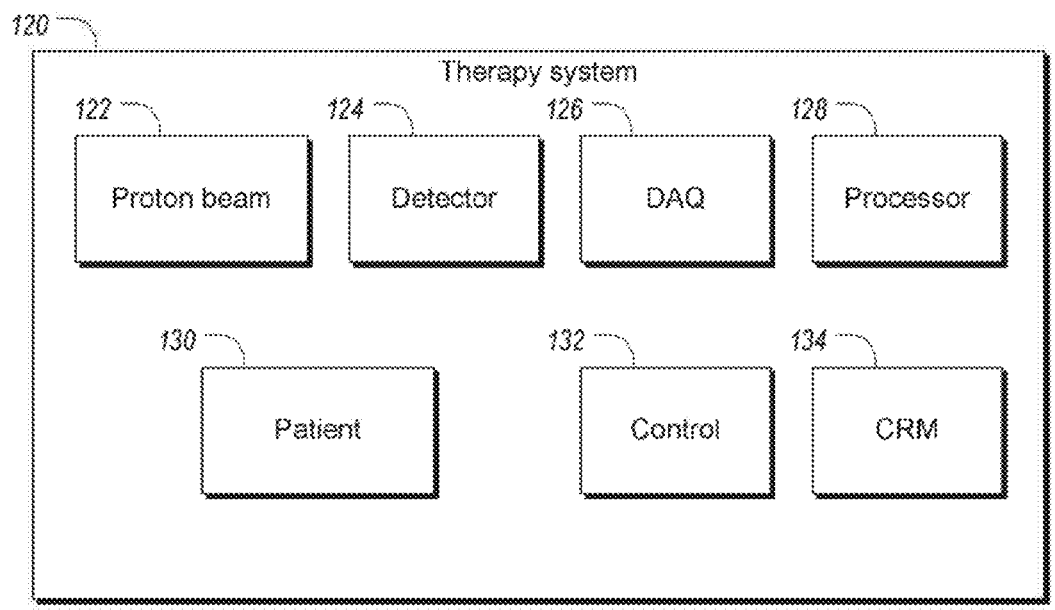

Although certain embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Described herein are methodologies and related systems for performing intensity-modulated radiation therapy. It will be understood that although some description herein is in the context of protons, ions, or other particles, one or more features of the present disclosure can also be implemented in radiation therapy applications using particles such as carbon ions or using electromagnetic radiation, such as x-rays. Some embodiments of the methodologies and related systems disclosed herein can be used with various delivery systems, including, for example, intensity modulated spot scanning, distal gradient tracking, distal edge tracking, pencil beam scanning, broad beam or passive scattering, or the like. Some embodiments of the methodologies and related systems can be used to treat a patient or to irradiate an object, and the treatment can be delivered in vivo or in vitro.

Unless explicitly indicated otherwise, terms as used herein will be understood to imply their customary and ordinary meaning. For example, pencil beam is a broad term and is to be given its ordinary and customary meaning to a person of ordinary skill in the art (e.g., it is not to be limited to a special or customized meaning), and includes, without limitation, a number of particles or photons of variable energy aimed at a patient or object from a given direction or from multiple directions. For example, a system can deliver a pencil beam to a patient by accelerating or receiving accelerated particles, mixing particles of various energies into a single beam, and directing the beam of particles at a patient.

Beamlet is a broad term and is to be given its ordinary and customary meaning to a person of ordinary skill in the art, and includes, without limitation, a stream of particles of a given initial energy and direction which can comprise part of a particle beam. For example, a system can accelerate particles to a particular energy using any suitable means, focus the stream of particles into a narrow stream, and direct the stream of particles either to a patient or to a system that can combine multiple particle beamlets into a particle beam.

Treatment plan is a broad term and is to be given its ordinary and customary meaning to a person of ordinary skill in the art, and includes, without limitation, a two- or three-dimensional dose distribution generated by one, two, or more than two pencil beams. Generally, a treatment plan can be overlaid with a treatment planning CT study. For example, a treatment plan can include doses to be delivered to volumes of interest within a patient or object. As another example, a treatment plan can include a configuration of pencil beams or beamlets adapted to deliver a defined, desired, or planned dose distribution to a patient or object.

Treatment planning system is a broad term and is to be given its ordinary and customary meaning to a person of ordinary skill in the art, and includes, without limitation, a module, system, computer program, hardware components, instructions on computer readable medium, or any combination of these configured to use a forward problem solver module or inverse problem solver module to calculate a dose distribution in a patient or object given characteristics of a beam, tissue composition, or both. For example, a treatment planning system can include one or more processors, memory, and/or computer readable medium configured to calculate doses delivered to tissue in a patient based at least in part on pencil beam energies, directions, and aiming points of one or more pencil beams. As another example, a treatment planning system can include a module adapted to calculate particle energy deposition in tissue based at least in part on characteristics of the tissue and properties of the pencil beam delivering the particles. As another example, a treatment system can include a system or module configured to determine a pencil beam configuration suitable for delivering particles or photons to volumes of interest such that doses to the volumes of interest fall within prescribed dose constraints.

FIG. 1A shows that in some embodiments, an imaging system 100 can be configured to perform proton computed tomography (pCT) operations and yield data that can be represented as a CT image of one or more portions of an object 110. The imaging system 100 can include a proton beam component 102 configured to deliver a beam of protons to the object 110. Controlling of various parameters of the proton beam, such as energy, direction and intensity can be achieved in a number of known ways.

The imaging system 100 can further include a detector component 104 configured to characterize protons that are incident on the object 110 as well as those that have passed through the object. In some implementations such a detector component 104 can be configured to characterize single protons.

The imaging system 100 can further include a data acquisition (DAQ) component 106 configured to read out signals from the detector component 104 so as to facilitate CT analysis. Amount of signal processing performed by the DAQ component 106 can vary.

In some implementations, signals from various detectors can be converted to digital signals by one or more analog-digital-converters (ADCs), and such digital signals can be read out under the control of a control component 112. Various control parameters such as event triggering, timing of event signals and readout, and resetting of detectors can also be controlled by the control component 112.

In some implementations, the imaging system 100 can further include a processor 108 that is configured to receive the digitized signals and perform analyses such as tracking of protons upstream and downstream of the object 110, as well as calculation of energies of downstream protons that passed through the object 110. In some implementations, tomographic reconstruction processing can also be performed by the processor 108. In other implementations, such tomographic reconstruction processing can be performed by a separate processor.

In some implementations, the imaging system 100 can further include a computer readable medium 114 configured to store information and/or executable instructions that facilitate operation of one or more components of the system 100. In some implementations, the computer readable medium 114 can include information and/or executable instructions that facilitate performance of one or more reconstruction processes. In some implementations, such information and/or executable instructions can be stored in a non-transitory manner.

In some implementations, one or more features of the present disclosure can be incorporated into a radiation therapy system 120 such as a proton or carbon beam therapy system. The therapy system 120 can include a proton or carbon beam component 122 configured to deliver a beam of protons or carbon ions to a patient 130. Such a beam of protons or carbon ions can be configured to yield a therapeutic effect on the patient. In some implementations, the proton beam component 122 can also be configured to yield proton beams that can pass through the patient so as to allow tomographic analysis as described above in reference to FIG. 1A. Examples of how such beams can be provided are described herein in greater detail.

The therapy system 120 can further include a detector component 124 configured to facilitate the treatment utilization of the proton beam 122. Such a detector component 124 can include devices that are configured to characterize protons that are incident on the patient 130 with desired parameters such as energy, direction and intensity. Such devices can be implemented in a number of known ways.

In some implementations, the detector component 124 can further include devices that are configured to facilitate pCT imaging functionalities such as those described in reference to FIG. 1A. In some embodiments, at least some of the therapy related detection devices can also be utilized for the purpose of pCT imaging. For example, beam detectors upstream of the patient can be utilized to characterize individual protons incident on the patient during operation in an imaging mode.

The therapy system 120 can further include data acquisition (DAQ) 126, control 132, processor 128 and computer readable medium 134 components configured to facilitate therapeutic and/or imaging modes of operation. The therapy system 120 can use the control 132, processor, and computer readable medium 134 to solve forward and inverse problems, create treatment plans, determine dose distributions, determine suitable settings to achieve a dose distribution, analyze representations of a patient to determine a treatment plan, receive user input, and the like.

The proton beam 122 of the therapy system 120 can be provided through the use of proton accelerators, such as cyclotrons, synchrotrons, linear accelerators, and the like. The proton beam 122 can be provided from multiple angles and at varying energies. The proton beam 122 can be a single beam of protons or multiple beams delivered in parallel or from multiple directions. In some embodiments, the therapy system 120 includes various components to shape and/or monitor the proton beam 122. For example, the therapy system 120 can include ionization chambers, magnets, scatterers, absorbers, range modulators, apertures, compensators, collimators, and the like.

The therapy system 120 can deliver the proton beam 122 to the patient through various means including broad beam or passive scattering, beam scanning, and/or intensity modulated proton therapy. Active or passive energy modulating components can be used by the therapy system 120 to control the depth of penetration of the proton beam 122. The therapy system 120 can include components configured to control the proton beam shape, direction, orientation, solid angle, fluence, cross-sectional area, and the like. As an example, a passive scattering therapy system can include one or more scattering surfaces to broaden and/or shape the proton beam 122 to deliver a desired dose to a targeted volume. In a beam scanning therapy system, the therapy system 120 can include magnets used to scan or steer the proton beam 122 across a target volume. In an IMPT system, the proton beam 122 can be magnetically and/or mechanically scanned over a target volume where the intensities of the beam spots on the target volume are modulated to deliver a planned or desired dose. In an IMPT system, the proton beam 122 can be delivered from one or more angles and/or positions wherein the intensities of the proton beam 122 at the various angles and/or positions is modulated to deliver a planned or desired dose.

In some embodiments of a therapy system 120, multiple proton beams 122 are delivered to a patient from multiple directions and angles. In some implementations, an individual proton beam comprises multiple proton beamlets where a beamlet is a group of protons with generally the same initial energy and direction. Proton beamlets can be formed using any suitable technique, including through the use of magnetic lenses.

The therapy system 120 can control, configure, or select energy distributions of the proton beams 122. A single proton beam 122 can comprise one or more proton beamlets. A proton beamlet is a group of protons with generally the same initial energy. To control, configure, or select the energy distribution of a proton beam 122, relative intensities of proton beamlets can be chosen such that the desired energy distribution for the proton beam 122 is achieved. The proton beamlets can be selected from a continuous energy range, or they can have discrete energy values. The intensities and/or energies of the proton beamlets can be actively or passively modulated by the therapy system 120. The energy distribution of a proton beam 122 can be configured to produce a SOBP such that structures in the patient 130 receive desirable doses.

The therapy system 120 can be configured to deliver proton beams from one or more angles and/or positions. In some embodiments, the therapy system 120 can have proton beams 122 at fixed relative locations. For example, the proton beams 122 can be coplanar lying along a circle, ellipse, square, rectangle, regular polygon, or other configuration, or the proton beams 122 can be non-coplanar. In some embodiments, the proton beams 122 are distributed along the therapy system 120 in an irregular pattern. In some embodiments, the proton beams 122 are steerable such that an orientation of the proton beam 122 relative to the patient 130 can change before, during, or after operation. Changing orientations for the proton beams 122 can include configuring an angle from which the proton beam 122 will be directed to the patient 130. In some embodiments, the therapy system 120 can dynamically change the positions and/or orientations of the beams 122. In some embodiments, the position of the patient 130 relative to the therapy system 120 can be altered.

Appropriately delivered proton, carbon ion, or other ions can provide a number of benefits in therapeutic applications such as cancer treatments. For example, proton therapy provides a benefit due at least in part to a sharp energy loss at the end of travel of a proton in a given material. Such a sharp energy loss has a relatively sharp peak called a Bragg peak and few of the particles having similar initial beam energy penetrate beyond such a depth. Depth locations of Bragg peaks can depend on the particle beam energy. Generally, a deeper Bragg peak can be achieved by a higher energy particle beam. Protons used for therapy can have energies in a range of about 70 MeV to 250 MeV and carbon ions up to 430 MeV/atomic mass unit.

Figure 2:
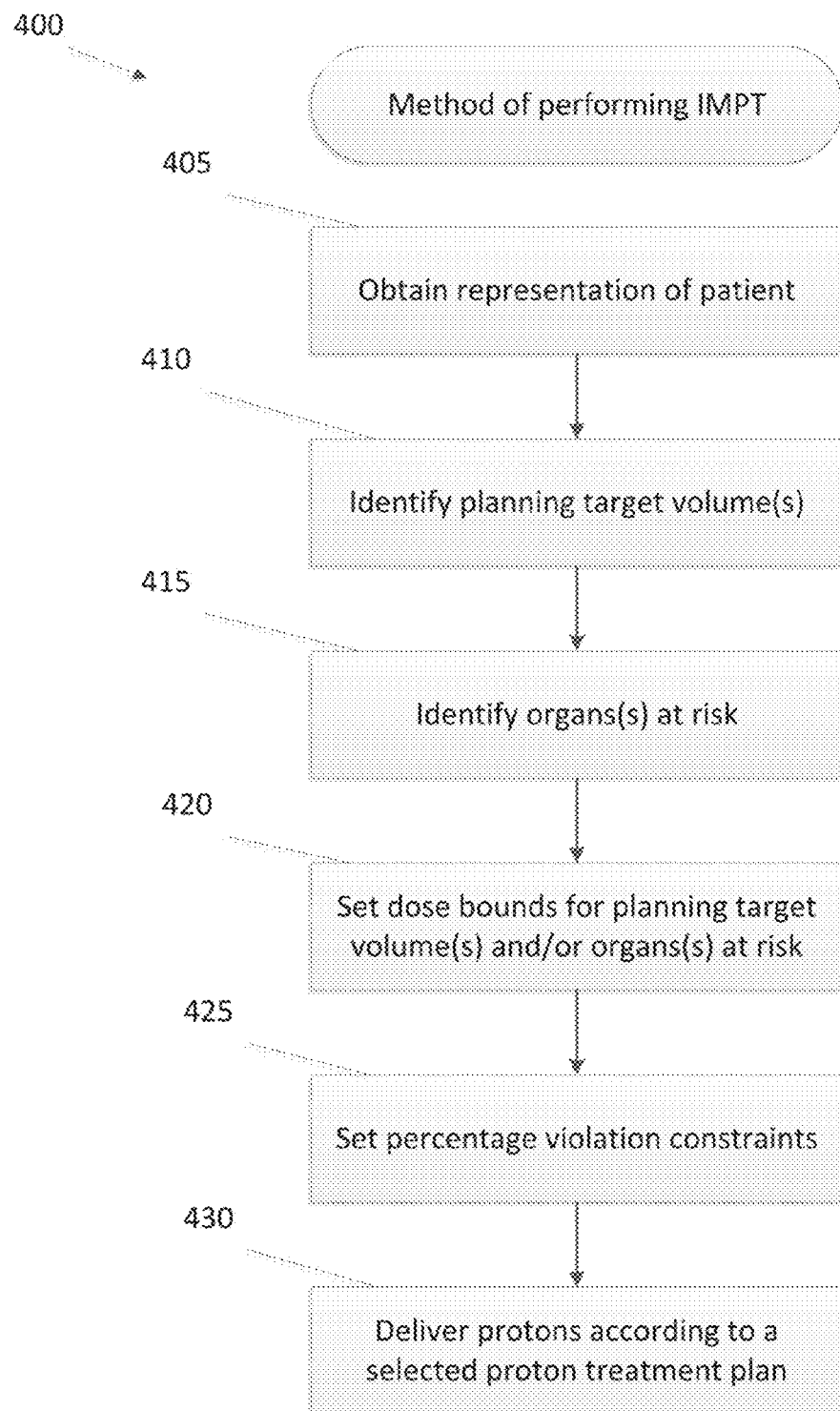
FIG. 2 shows a method for performing IMPT.
Figure 3:
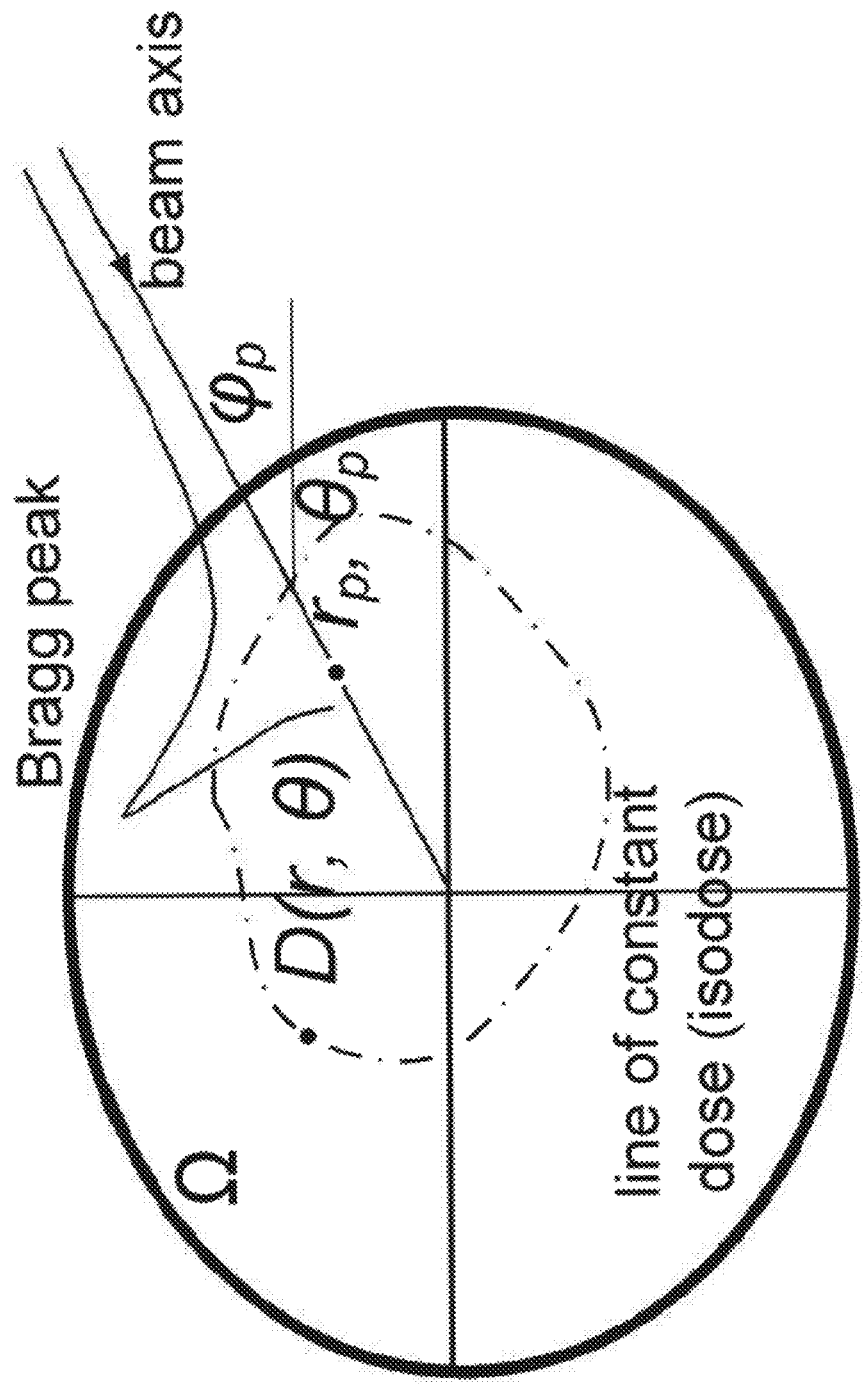
FIG. 3 shows an example of how proton therapy is applied.

FIG. 2 illustrates a flow chart of an example method 400 that can be implemented to perform proton therapy on a patient. For ease of description, the process 400 is described as performed by a proton therapy system. The proton therapy system can be a system configured to deliver protons such as the therapy system 120 described herein. The proton therapy system can be different from the therapy system 120, including more, fewer, and/or different components. The proton therapy system can include multiple components, each of which can be configured to perform one or more of the steps in the process 400. Each step of the process 400 can be performed by a single component or multiple components. In some embodiments, the proton therapy system includes modules configured to perform one or more steps in the process 400.

In block 405, the proton therapy system obtains a representation of the patient that is to receive proton therapy. The representation can be, for example, one or more digital or analog images, a sequence of images, a video, a representation of densities of the patient as a function of position in the patient, a representation of another biological property of the patient as a function of position, or any combination of these. In some embodiments, the representation is created using functional imaging, such as X-ray CT, proton CT (pCT), positron emission tomography (PET), magnetic resonance imaging (MRI), and/or spectroscopic imaging. As described more fully herein, it can be advantageous to use a representation derived from pCT to reduce possible uncertainties in proton penetration ranges. In some embodiments, the proton therapy system analyzes the obtained representation to create a map or image of structures on and/or within the patient. For example, the proton system can analyze the representation to create a two- or three-dimensional plot of the relative densities of structures on and/or within the patient. In some embodiments, the proton system creates one or more images from the representation which can be presented to a user, oncologist, dosimetrist, physicist, operator, physician, patient, or the like.

In some embodiments, the representation can be used to obtain information related to biological properties of targeted structures and/or surrounding structures. Such biological information can include, for example, composition, clonogen density, tumor hypoxia, proliferation, and/or radiosensitivity. In some implementations, non-uniform dose distributions across a targeted volume can benefit from knowledge of biological information to improve or optimize a treatment plan. Selective targeting of sub-volumes within a target can increase the probability of destroying the targeted cells and/or reduce complications to non-targeted tissues or organs at risk. In some implementations, a substantially uniform dose is desired across the targeted volume.

In block 410, one or more target volumes can be identified. The target volumes can be any volume that includes cells whose destruction is desired, and can include, for example, cancerous cells, dysplastic cells, tumors, lesions, or other cells or tissue. In some embodiments, the target is automatically identified by the proton therapy system based at least in part on the obtained representation. The proton therapy system can be configured to identify the target based at least in part on one or more criteria such as, for example, location, density, size, temperature, blood flow, oxygenation, shape, other biological properties, other physical properties, or any combination of these. In some embodiments, the proton therapy system receives input from a user to identify the target. Identifying the target can include, for example, indicating which structure, structures, or portion of a structure is the target volume; mapping the target volume; localizing the target volume on or within the patient; extracting biological information about the target volume; or any combination of these.

In some embodiments, identifying the target includes dividing the target volume into sub-volumes. Target sub-volumes can be selected and/or delineated based at least in part on, for example, physical properties, biological properties, practical concerns, geometrical considerations, or any combination of these. The proton therapy system can identify target sub-volumes based at least in part on the obtained representation, biological information, and/or data received from a user. In some embodiments, the proton therapy system identifies the target sub-volumes according to standards set by the International Commission of Radiation Units (ICRU). For example, the Gross Target Volume (GTV) can be defined as the gross palpable, visible, or clinically-demonstrable disease; the Clinical Target Volume (CTV) can include the GTV plus any margin for sub-clinical malignant disease; the Internal Target Volume (ITV) can include the CTV plus an internal margin for organ motion; and the Planning Target Volume (PTV) can include the CTV or the ITV plus any setup margin for uncertainties related to patient positioning and/or alignment of therapeutic beams. In some embodiments, other sub-volume identification schemes are used. For example, a target sub-volume can be defined based at least in part on proton energy deposition characteristics, proximity to an organ at risk, and/or tissue composition.

In block 415, the proton therapy system identifies one or more organs at risk. An organ at risk can include any organ or structure in the patient where cell or tissue destruction is less desirable or would be harmful to the patient. The positions of the identified organs at risk relative to the target volume can be identified and mapped in two or three dimensions through the use of functional imaging. Similar to the identification of the target volume in block 410, the proton therapy system can identify organs at risk automatically, semi-automatically, and/or based at least in part on data received from a user. Identifying organs at risk can include, for example, indicating which structure, structures, or portions of a structure is an organ at risk; mapping the organs at risk; localizing the organs at risk within the patient; extracting biological information about the organs at risk; or any combination of these.

In some embodiments, identifying organs at risk includes dividing the organs at risk into sub-volumes. The sub-volumes of organs at risk can be selected and/or delineated based at least in part on, for example, physical properties, biological properties, practical concerns, geometrical considerations, or any combination of these. The proton therapy system can identify organ at risk sub-volumes based at least in part on the obtained representation, biological information, and/or data received from a user. In some embodiments, the proton therapy system identifies the organ at risk sub-volumes according to standards set by the ICRU. For example, the Organ at Risk (OAR) can be defined as normal tissue or organ whose radiation sensitivity can significantly influence treatment planning and/or prescribed dose wherein the OAR should be delineated in its entirety or within stated anatomical or geometrical boundaries; the Planning OAR Volume (PRV) can include the OAR plus any margin for internal organ motion and/or setup margin for uncertainties related to patient positioning and alignment wherein the PRV should be delineated even where it overlaps PTVs or other PRVs. In some embodiments, other sub-volume identification schemes are used. For example, an organ at risk sub-volume can be defined based at least in part on proton energy deposition characteristics, proximity to a target volume, and/or tissue composition. In some implementations, any volume that is not classified as either a target or an organ at risk can be designated as a Remaining Volume at Risk (RVR).

In block 420, the proton therapy system sets dose bounds and/or constraints for volumes and/or sub-volumes of interest. The volumes and sub-volumes of interest can include target volumes, target sub-volumes, organ at risk volumes, organ at risk sub-volumes, remaining volumes at risk, other volumes, other sub-volumes, or any combination of these. An operator, user, dosimetrist, physicist, oncologist, or physician can use dose constraints to account for tissue tolerance, limit or control the exposure of normal tissue to radiation, specify desired levels of radiation for targeted tissue, and the like. To accomplish one or more of these goals, the proton therapy system can set dose constraints based at least in part on, for example, tissue properties of organs at risk and/or targeted volumes, relative positioning of volumes and sub-volumes, percentage of volume or sub-volume with diseased cells, patient movement, volume of interest variation with time, range uncertainties in proton penetration depth, or any combination of these.

In some embodiments, the proton therapy system selects and sets the dose constraints. In some embodiments, the proton therapy system receives dose constraints from a user, operator, physician, or the like. Dose constraints can be selected based at least in part on a desired therapeutic result or effect, radiosensitivity of the volumes and/or sub-volumes of interest, input from a physician, operating characteristics of the proton therapy system and associated proton beam, proximity and positioning of surrounding structures, avoiding an undesired effect, prescribed standards, nature of targeted cells, properties of targeted cells, or any combination of these. In some embodiments, the proton therapy system sets a maximum dose constraint, a minimum dose constraint, or both for one or more volumes or sub-volumes of interest.

In block 425, the proton therapy system sets one or more percentage violation constraints for use in delivering protons to the patient. Proton therapy systems can provide one, two, or more than two percentage violation constraints for the treatment of a patient. One or more of the provided percentage violation constraints can be selected to perform radiation therapy for a patient. The number of percentage violation constraints selected can affect, for example, dose conformity, integral dose, target coverage, or dose to organs at risk. In some implementations, the number of percentage violation constraints can be selected to achieve a desired therapeutic result, such as, for example, increasing dose conformity and reducing the integral dose. In some implementations, reducing the number of percentage violation constraints may be desirable to reduce the time and/or computing power to calculate feasible, desirable, or optimal proton treatment plans. In some implementations, users select a proton treatment plan from plans presented by the proton therapy system. In such a scenario, it can be advantageous to select a number of percentage violation constraints such that fewer options are presented to the user to avoid overwhelming the user due to the number of possible plans.

In block 430, the proton therapy system creates a proton treatment plan. The proton treatment plan can include a two- or three-dimensional dose distribution that could be generated by selected proton beams. The proton therapy system can present the proton treatment plan to a user, operator, dosimetrist, oncologist, physicist, physician, patient, technician, or the like through a display apparatus. In some implementations, the system presents the treatment plan overlaid on the obtained representation. For example, the system can display one or more images obtained from pCT and overlay the dose distribution on the one or more images such that the user can visually analyze the treatment plan. The system can be configured to display, for example, projected doses to volumes and sub-volumes of interest, indicators of the boundaries of volumes and/or sub-volumes of interest, labels identifying volumes and/or sub-volumes of interest, dose volume histograms, treatment plan quality or conformity indicators, or any combination of these.

The proton therapy system can include a forward problem solver module to assist in creating proton treatment plans. The forward problem solver module can be used to calculate a dose distribution in a patient as a function of properties of a proton beamlet. The dose distribution generated by the proton beamlet depends at least in part on the composition of the patient and the energy, orientation, and direction of the proton beamlet. In some implementations, the forward problem solver module incorporates characteristics of proton beamlets that influence the calculated dose distribution. The forward problem solver module can be used to calculate a dose distribution based on multiple proton beamlets, thus generating a proton treatment plan.

The proton therapy system can include an inverse problem solver module to assist in creating proton treatment plans. The inverse problem solver module can be used to calculate a proton beam configuration that attempts to achieve a prescribed dose distribution. Given a prescribed dose distribution, the inverse problem solver module can be configured to generate possible proton beam configurations that satisfy the prescription. The proton beam configurations can include the number of beams, the distribution of proton energies in the beams, the orientation of the beams, the direction of the beams, the duration of therapy, or any combination of these. As described more fully herein with reference to FIGS. 7 and 8, the inverse problem solver module can be used to generate feasible proton treatment plans. A feasible proton treatment plan is a plan that satisfies the dose constraints set in block 420.

In some embodiments, the proton therapy system includes an improvement module for improving or optimizing proton treatment plans. As described more fully herein below, the improvement module can attempt to improve or optimize aspects of one or more proton treatment plans based at least in part on weighted sums of doses, min-max dose functions, Pareto optimality, or any combination of these. In some embodiments, the proton therapy system accepts input from a user to include in the improvement module. For example, the user can choose weighting factors to enhance certain aspects of a treatment plan, such as dose-sparing for normal tissue or increasing tumor control probability, or the weighting factors can be chosen to emphasize a balance between improving the tumor control probability and sparing normal tissue.

In block 435, the proton therapy system delivers protons according to a selected proton treatment plan. In some implementations, the proton therapy system automatically selects the proton treatment plan according to desired, defined, default, or selected criteria. For example, the system can automatically select the proton treatment plan that delivers the maximum dose to the target volume while the maximum dose to any organ at risk is below a defined threshold. As another example, the system can automatically select the proton treatment plan that delivers a dose to one or more organs at risk that is below a threshold dose while the minimum dose to the target volume exceeds a defined threshold. In some implementations, the proton therapy system selects a proton treatment plan based at least in part on input from a user. For example, the proton therapy system can present to a user treatment plans from which the user can make a selection.

Forward Problem Solver

As described herein, a forward problem solver can be used to calculate dose distributions based at least in part on proton beamlet characteristics. The forward problem solver can be a module in the proton therapy system or in another system. The forward problem solver can be implemented using one or more processors, memory, and computer readable medium. The forward problem solver can be configured to produce a solution to a forward problem in near real-time.

In proton therapy, a forward problem can comprise calculating an output dose based at least in part on an input proton beamlet. The problem can be set forth as follows: given a radiation intensity function of proton beamlets, find the dose function for a cross-section within an object. A proton beamlet can be represented by a real-valued function $\rho_p(r_p, \varphi_p, \theta_p)$, where $r_p$, $\theta_p$ is the location of the Bragg peak on the beam axis, $\varphi_p$ is the angle of the beam axis with the 0-degree axis of the coordinate system, and $\rho_p$ is the intensity of the beam. A dose in the central beam axis plane, defined on a known object cross-section $\Omega$, can be represented by the real-valued, non-zero function $D(r, \theta)$, represented in polar coordinates. Thus, the forward problem comprises finding $D(r, \theta)$ for all $(r, \theta)$ within the cross-section $\Omega$, or $D(r, \theta) = \Delta[\rho_p(r_p, \varphi_p, \theta_p)](r, \theta)$ where $\Delta$ is the dose operator that relates the dose function to the radiation intensity function. The dose operator generally is not represented by a closed-form analytic relation between the intensity function and the dose function. In some embodiments, a forward problem solver can be configured to calculate the dose function, D, from the intensity function, ρ.

In some embodiments, the forward problem solver incorporates characteristics of proton beamlets to calculate the dose function, D. For example, the forward problem solver can include the absorbed distribution of protons in water in the calculations. The forward problem can include the cylindrical symmetry of the dose distribution around the central beam axis, as another example. Furthermore, the forward problem solver can include the shape of the central beam axis dose distribution, the Bragg peak curve as described herein. As another example, the forward problem solver can model the lateral dose profile as a Gaussian function with a depth-dependent width, and can include non-Gaussian tails. As another example, the forward problem solver can scale the beamlet dose profiles linearly with the beam intensity or proton fluence. In some embodiments, the forward problem solver scales the profiles of the proton beamlets for non-uniform tissues that may be different from water. For example, the forward problem solver can scale the profiles according to the relative stopping power and/or relative scattering power of the tissue. By combining the doses from proton beamlets to be used in a proton treatment plan, the forward problem solver can calculate the dose distribution of a complete proton treatment plan.

As described herein, an inverse problem solver can be used to calculate a proton beam configuration that delivers a prescribed dose to an object. The inverse problem to be solved for a proton therapy system can be more complex than the inverse problem in other radiation therapy systems because there are a greater number of degrees of freedom due to the capability of a proton system to configure the depth of the Bragg peak of a proton beamlet by selecting a particular energy. Thus, approaches to solving the inverse problem for proton therapy systems can involve comparatively more computational resources, optimization routines, or solution strategies. As a result, solutions to the inverse problem for proton therapy systems can provide relatively higher dose conformity and tumor control probability and lower integral dose and normal tissue complication probability compared to other radiation therapy systems.

The inverse problem solver can be a module in the proton therapy system or in another system. The inverse problem solver can be implemented using one or more processors, memory, and computer readable medium. In some implementations, the inverse problem solver can be configured to produce a solution to an inverse problem in near real-time.

Convex Feasibility Problem

In IMPT systems, the inverse problem comprises calculating feasible particle beam configurations that result in dose distributions that satisfy dose constraints. In some implementations, IMPT can be performed utilizing one or more feasibility seeking methods. For an imaging situation that yields an intersection of a finite family of convex sets (e.g., the example intersection region Q resulting from a set of convex sets 610 in FIG. 7E), a plurality of solutions can exist. In a convex feasibility problem (CFP) methodology, a solution among such a number of solutions can be searched for and obtained; and such a solution can correspond to a point within the intersection region.

In some implementations, the CFP can be solved as follows. If an intersection Q of closed convex sets $Q_1$, $Q_2, \ldots, Q_p \subseteq R^n$ exists, then a point $x^*$ exists on Q. Generally, $Q_i$ can be expressed as $Q_j = \{x \in R^n | f_j(x) \leq v_j\}$, for all $j \in J := \{1, 2, \ldots, p\}$, where $f_j : R^n \to R$ are convex functions and vj are real numbers. In embodiments where Q exists as described, the CFP can be solved by finding a point $x^* \in Q := \cap_{j \in J} Q_j$. In embodiments where $Q = \emptyset$, the CFP is inconsistent and can be solved a different way, as described below. In certain cases, the addition of constraints that are integers can turn a CFP into a mixed integer feasibility problem. Such problems may need to be solved differently (see below).

For IMPT using CFP methodology, desirable performance can be based on factors such as use of an efficient feasibility seeking projection method. In some configurations, determining a proton intensity vector includes finding a feasible solution having a reduced value of a given merit function. In some implementations, superiorization can be used to find a superior solution with respect to some merit function, which is also a feasible solution of corresponding CFP sets. A superior solution can be a feasible solution of the CFP for which the value of the merit function, with respect to which one superiorizes, is smaller (but not necessarily minimal) than the value of this function at a feasible point that would have been reached if the superiorization process would not have been applied.

Inverse Problem Solver

If $D(r, \theta)$ represents a prescribed dose function in a known cross-section Ω of an object, then the inverse problem comprises finding a radiation intensity function $\rho_p(r_p, \varphi_p, \theta_p)$ such that $\rho_p(r_p, \varphi_p, \theta_p) = \Delta^{-1}[D(r, \theta)]$ where $\Delta^{-1}$ is the inverse dose operator that relates the radiation intensity function to the dose function.

Figure 4:
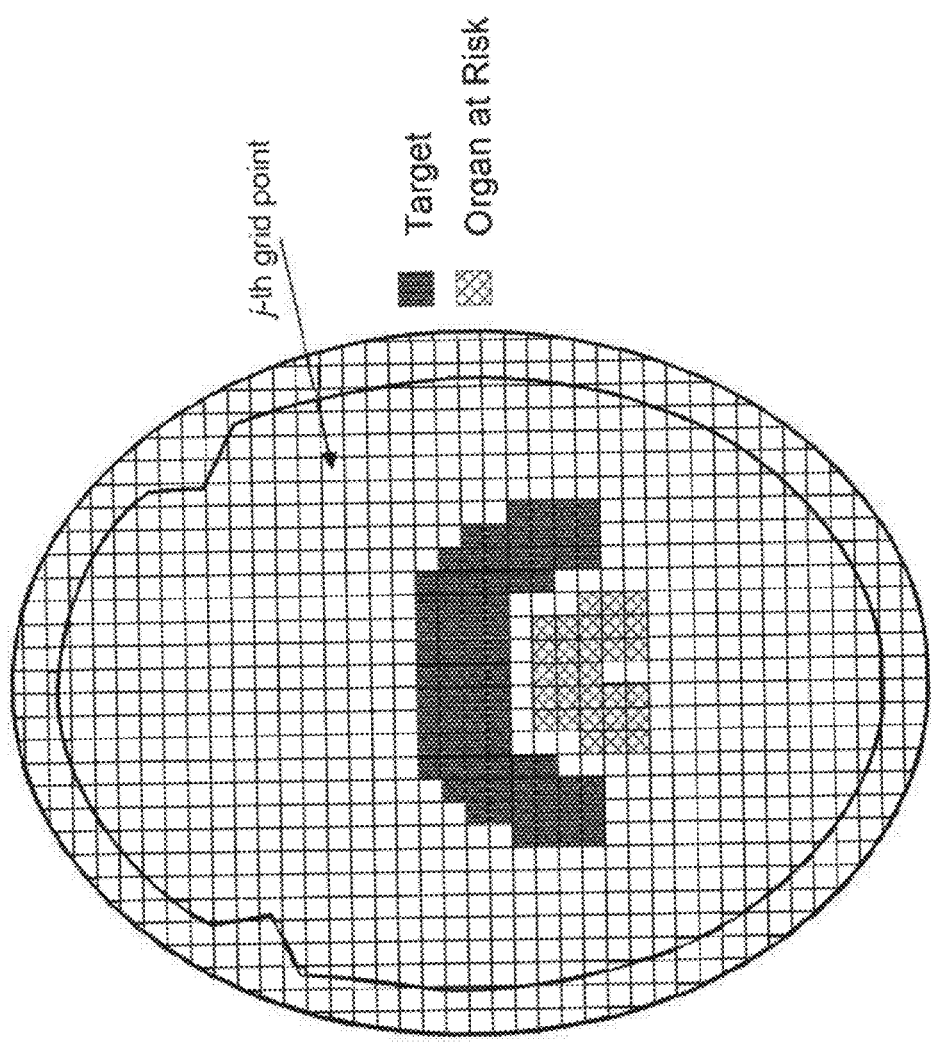
FIG. 4 shows how volumes can be divided.

The inverse problem solver can be implemented using a discrete model. Referring to FIG. 4, the discrete model includes dividing an object cross-section into a discrete grid of dose calculation points. In some embodiments, the discrete grid points represent voxels in the object. From the grid, a number of dose calculation points are chosen for which a dose will be calculated. For example, the inverse problem solver can select J points represented by the polar-coordinate pairs $(r_j, \theta_j)$, where j goes from 1 to J. In addition, the discrete model can include defining a discrete grid of beam aiming points within the target and a discrete grid of beam directions, from which the inverse problem solver selects a number of beamlets. For example, the inverse problem solver can select I beamlets represented by the triplets $(r_i, \varphi_i, \theta_i)$ where i goes from 1 to I. In some implementations, the discrete grid of beam directions is equally spaced. In some implementations, the grid of dose calculation points differs from the gird of beam aiming points.

The discrete inverse problem can be set forth by defining $a_{ij}$ to be the dose delivered by the i-th beamlet of unit intensity (or proton fluence) to the j-th dose grid point or voxel. In addition, $x_i$ can be defined as the actual intensity of the i-th beamlet, or the solution the inverse problem solver is seeking. Furthermore, $b_j$ can be defined as the prescribed dose to the j-th dose grid point. As such, the discretized inverse problem becomes finding a proton beamlet vector $x^*$ that solves the linear problem:

$$A^T x^* = b, \text{ where } x^* \geq 0 \quad (1)$$

where the matrix AT comprises doses of the I unit intensity beamlets to the J object grid points. In some implementations, the inverse problem solver can use a continuous model to solve the inverse problem. For example, the discrete vectors x and b can be represented as two- or three-dimensional functions of proton beam intensities, x(r), and prescribed doses, b(r), and the matrix AT can be represented as an operator A that operates on the function x(r) to transform the beam intensities function, x(r), into the prescribed dose function b(r).

In some embodiments, the inverse problem solver can use a forward problem solver to calculate the elements of the matrix A. For example, the forward problem solver can calculate a dose to a specified grid point or voxel within the object cross-section based at least in part on a proton beamlet having unit intensity and having a triplet $(r_i, \varphi_i, \theta_i)$ representing the location of the Bragg peak in polar coordinates and the beam direction, as described more fully herein above. Thus, the inverse problem solver can construct the matrix A for permutations of dose grid points and beamlets using the forward problem solver.

The grid for the beam aiming points can be the same size as, finer than, or coarser than the grid of dose calculation points. In some embodiments, the size of the grid of beam aiming points is related to the size of the proton beamlets. For example, the size of the grid of beam aiming points can be related to the lateral penumbra of a proton beamlet, where the lateral penumbra can be defined as the lateral extent of a dose from a central beam axis.

In some embodiments, the inverse problem solver can select a limited quantity of fixed beam directions to reduce the complexity of the problem. For example, the inverse problem solver can select at least 1 beam direction and/or less than or equal to 50 beam directions, at least 2 beam directions and/or less than or equal to 25 beam directions, at least 3 beam directions and/or less than or equal to 10 beam directions, or at least 4 beam directions and/or less than or equal to 8 beam directions. For each beam direction, the proton therapy system can direct the beam to the beam aiming point by magnetic scanning, mechanical scanning, moving the patient relative to the beam spot, or using other suitable techniques or combination of techniques.

Method of Solving an Inverse Problem

Figure 5:
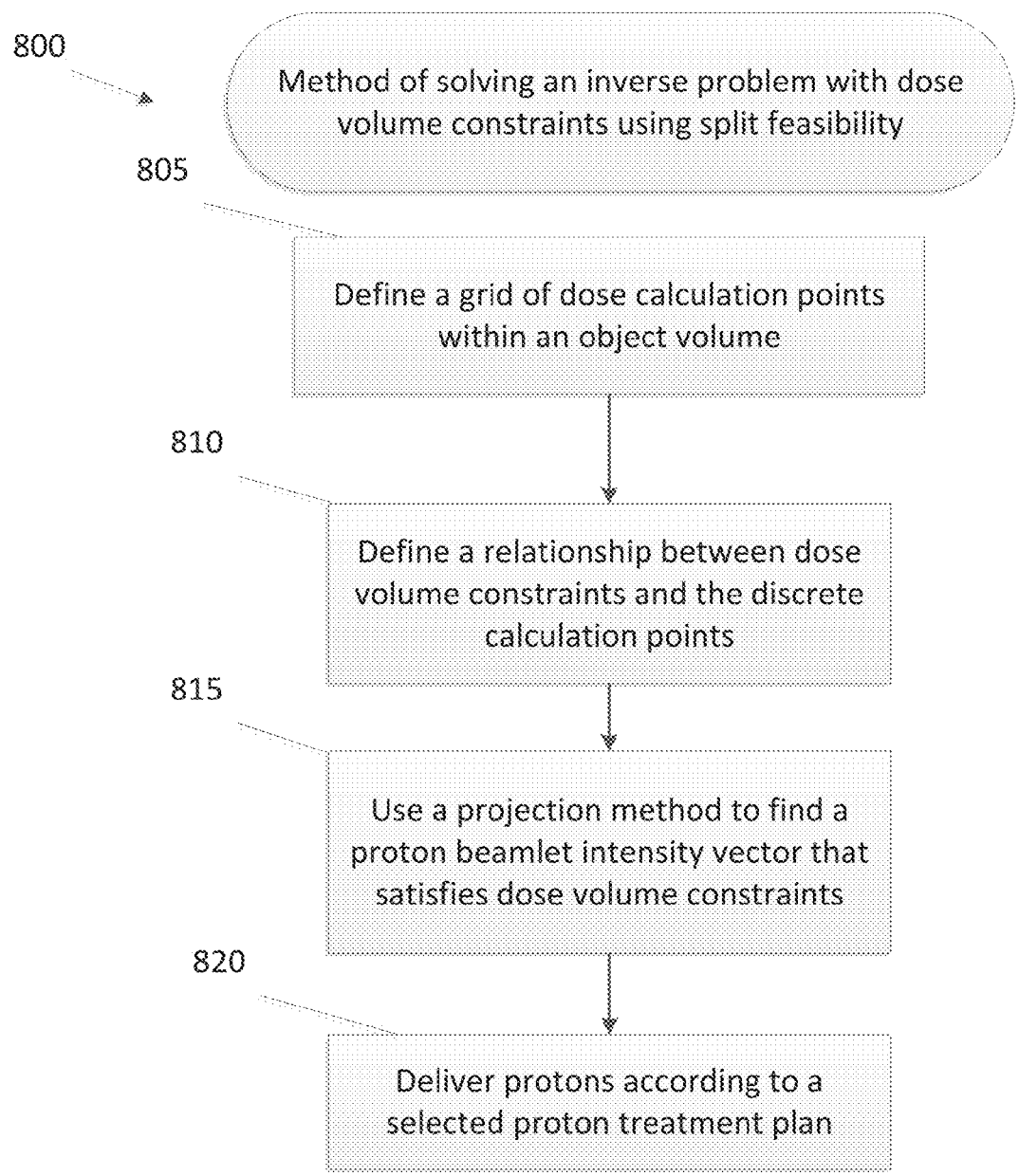
FIG. 5 shows a method for solving an inverse problem with dose volume constraints.
Figure 6:
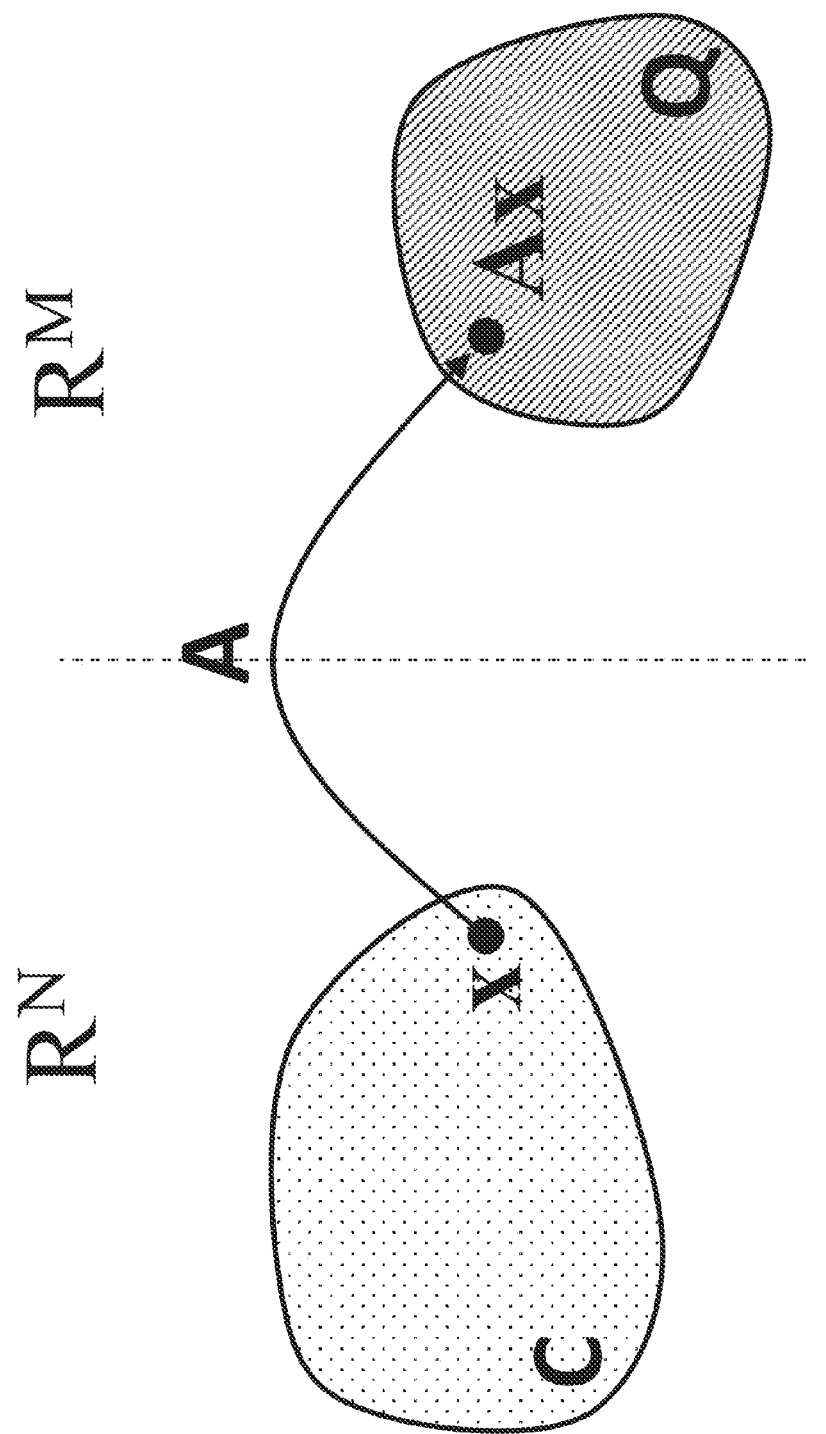
FIG. 6 schematically shows how a projection can be done.

FIG. 5 illustrates a flow chart of an example method 800 of solving an inverse problem using a feasibility approach. The feasibility approach alters equation (1) above to be a pair of inequalities representing upper and lower dose bounds. The equation (1) thus becomes:

$$\underline{D} \leq A^T x^* \leq \overline{D}, \text{ where } x^* \geq 0 \quad (2)$$

where $\underline{D}$ is a vector representing lower dose bounds and $\overline{D}$ is a vector representing upper dose bounds. Any solution to the above inequalities is deemed a feasible solution by the inverse problem solver. The upper and lower dose bounds can be prescribed by the proton therapy system and/or selected by a user. As such, any resulting treatment plan based on a feasible solution could be implemented by the user as it conforms to the prescribed dose constraints.

In block 805, the inverse problem solver defines a grid of dose calculation points within the object volume. In some embodiments, the grid points are voxels within the object volume. As described above with reference to FIG. 4, the grid of dose calculation points represents discrete points in an object cross-section for which a dose calculation will be made. Additionally, the inverse problem solver can define beam aiming grid points in the object cross-section. The beam aiming grid points can coincide with the dose calculation grid points or they can be finer or coarser.

In block 810, the inverse problem solver sets a relationship between dose volume constraints and the discrete calculation points. In some embodiments, the dose volume constraints are set automatically by the inverse problem solver based at least in part on biological, physical, geometrical, and/or physiological information. In some embodiments, the dose volume constraints are set according to input received from a user. For each dose grid point or voxel defined in block 805, a dose volume constraint can be set by the inverse problem solver. In some embodiments, an upper dose volume constraint, lower dose volume constraint, or both is set for each dose grid point. In some embodiments, the dose volume constraints are grouped according to volumes and/or sub-volumes of interest. For example, the inverse problem solver can set dose volume constraints uniformly for dose grid points that fall within the same target sub-volume, target volume, organ at risk sub-volume, organ at risk volume, remaining volume, or other volume.

In block 815, the inverse problem solver uses projection method to find a proton beamlet intensity vector that satisfies the dose volume constraints, as described herein. In some configurations, it also sets beam directions. The inverse problem solver can select the beam directions based at least in part on a configuration of proton beams of a therapy system, patient positioning, efficiency considerations, practical considerations, computational considerations, or any combination of these. In some embodiments, the inverse problem solver selects the beam directions based at least in part on input received from a user. The selection of beam directions can reduce the complexity of the inverse problem. Reducing the complexity can result in faster computational times and fewer possible treatment plans for a user or physician to review.

In block 820, the inverse problem solver causes the IMPT system to deliver protons according to a selected proton treatment plan, as described herein. For example, where there are J dose grid points and I proton beamlets, the problem can be expressed as:

$$\underline{D}_j \leq \Sigma_{i=1,\ldots,I} a_{ij} x_i \leq \overline{D}_j, j=1, 2, \ldots J \text{ and } 0 \leq x_i \leq x_{max}, \quad i=1, 2, \ldots I \quad (3)$$

where the subscript j refers to a dose grid point or voxel and the subscript i refers to a proton beamlet.

In some embodiments, the inverse problem solver can be configured to find a proton beamlet intensity vector x* that satisfies groups of constraints. If G is defined as the set of all dose grid points or voxels, subsets of G can be defined such that the inverse problem solver assigns dose constraints (e.g., dose volume constraints) for each subset. For example, $B_l$ can be a subset of G representing L organs at risk, where l=1, 2, . . . L. Dose constraints can be assigned to each organ at risk, or $B_l$, and can be represented by upper dose constraint $\overline{b}_l$ and lower dose constraint $\underline{b}_l$. In some embodiments, $\overline{b}_l$ is greater than or equal to zero and $\underline{b}_l$ is zero. As another example, $T_q$ can be a subset of G representing Q target volumes, where q=1, 2, . . . Q. Dose constraints can be assigned to each target volume, or $T_q$, and can be represented by upper dose constraint $\overline{t}_q$ and lower dose constraint $\underline{t}_q$. In some embodiments, both $\overline{t}_q$ and $\underline{t}_q$ are greater than zero. As another example, C can be a subset of G representing a remaining volume at risk, e.g., dose grid points that are neither part of $B_l$ nor $T_q$. Dose constraints can be assigned to the remaining volume at risk, or C, and can be represented by upper dose constraint $\overline{c}$ and lower dose constraint $\underline{c}$. In some embodiments, $\overline{c}$ is greater than or equal to zero and $\underline{c}$ is zero. The inverse problem solver can be configured to solve an inverse problem similar to equation (3) with an inequality incorporating the corresponding constraints for each defined subset.

In some embodiments, one or more of the organs at risk in the subset $B_l$ can be divided into sub-volumes. Dividing organs at risk into sub-volumes can enable more efficacious proton treatment plans by reducing the integral dose to normal tissue and providing greater control over dose distributions in proton therapy. Organ at risk sub-volumes can be defined, for example, according to biological parameters, physiological parameters, geometrical considerations, relative positioning of structures, practical considerations, or any combination of these.

In some embodiments, an organ at risk is divided into sub-volumes comprising non-overlapping, relative fractional volumes, the sub-volumes being defined based at least in part on distance relative to a feature of interest, such as a target volume. An example procedure to divide an organ at risk $B_l$ into sub-volumes can include identifying a target volume $T_q$ that is the closest target volume to the organ at risk. A number $S_l$ of non-overlapping, fractional sub-volumes $f_{ls}$, where $s=1, 2, \ldots S_l$, can be defined for the organ at risk such that each fractional volume $f_{ls}$ is less than one and the sum of all fractional volumes is equal to one. The sub-volumes can be defined by ordering discrete grid points or voxels within the organ at risk $B_l$ according to their distance from the target volume $T_q$. Subsets can be created using the ordered points such that the first subset contains a number of grid points approximately corresponding to the fraction $f_{1s}$ of the total number of dose grid points within the organ at risk, the second subset contains the fraction $f_{2s}$, and so on. In some embodiments, the organ at risk $B_l$ is divided into sub-volumes based at least in part on proximity to a convex hull of any feature of interest, such as target volume $T_q$, not solely based on proximity to the closest target volume. In some embodiments, subsets of the organ at risk $B_l$ are created based at least in part on other criteria, such as, density of tissue, proximity to other organs at risk, patient positioning, beam configuration, uncertainties in proton ranges, uncertainties in positioning of structures, organ movement, or any combination of these.

In some embodiments, one or more target volumes in the subset $T_q$ can be similarly divided into sub-volumes comprising non-overlapping, relative fractional volumes. The division of target volumes into sub-volumes can lead to greater dose conformity, less integral dose, greater tumor control probability, or lower normal tissue complication probability. Target sub-volumes can be defined, for example, at least in part according to biological parameters, physiological parameters, geometrical considerations, relative positioning of structures, practical considerations, or any combination of these.

For example, a target volume $T_q$ can be divided into non-overlapping, relative fractional volumes based at least in part on distance to the boundary of the target volume. An example procedure to divide a target volume $T_q$ into sub-volumes can include identifying an exterior boundary of the target volume. Prescribed relative fractions $f_{qs}$ can be defined that divide the target volume $T_q$ into $S_q$ non-overlapping sub-volumes, where the fractions $f_{qs}$ are all less than one and sum to one. The sub-volumes can be defined by ordering discrete grid points within the target volume $T_q$ according to the shortest distance to the outer boundary of the target volume. Subsets can be created from the ordered points such that the ratio of the number of grid points in the first subset to the total number of grid points within the target volume is approximately equal to the first prescribed relative fraction, $f_{q1}$. A similar procedure can be repeated for each target sub-volume. In some embodiments, subsets of the target volume $T_q$ are created based at least in part on other criteria, such as, density of tissue, proximity to organs at risk, patient positioning, beam configuration, uncertainties in proton ranges, uncertainties in positioning of structures, organ movement, or any combination of these.

As an example, a target volume $T_q$ can be divided into two sub-volumes. The first sub-volume can include approximately 5% of the total number of grid points or voxels, and the second can contain approximately 95%. The first sub-volume can be referred to as a peripheral fractional volume and can include approximately 5% of the grid points closest to the convex hull of the target volume $T_q$. The second sub-volume can be referred to as a central fractional volume and can include the remaining dose grid points.

A generalized representation of the discrete inverse problem incorporating target and organ at risk sub-volumes can be expressed as follows:

$$\underline{b}_{ls} \leq \Sigma_{i=1,\ldots,I} a_{ij} x_i \leq \overline{b}_{ls}, \text{ for all } j \text{ in } B_{ls}, l=1, 2, \ldots L \text{ and } s=1, 2, \ldots S_l \quad (4a)$$

$$\underline{t}_{qs} \leq \Sigma_{i=1,\ldots,I} a_{ij} x_i \leq \overline{t}_{qs}, \text{ for all } j \text{ in } T_{qs}, q=1, 2, \ldots Q \text{ and } s=1,2,\ldots S_q \quad (4b)$$

$$\underline{c} \leq \Sigma_{i=1,\ldots,I} a_{ij} x_i \leq \overline{c}, \text{ for all } j \text{ in } C \quad (4c)$$

$$0 \leq x_i \leq x_{max}, \text{ for all } i=1, 2, \ldots I \quad (4d)$$

where the various underlined and overlined vectors respectively represent lower and upper dose bounds for the corresponding volumes and sub-volumes.

In some cases, a linear interval feasibility problem (LIFP) can be solved using the IMPT inverse problem solver (e.g., processor). Without being limited by theory, an LIFP problem can be described as follows. A solution $x^* \in R^n$ exists if it can be supplied to fulfill the following inequalities:

$$0 \leq A_1 x \leq b^1 \quad (5a)$$

$$b^2 \geq A_2 x \geq b^2 \quad (5b)$$

$$0 \leq A_3 x \leq b^4 \quad (5c)$$

$$x \geq 0 \quad (5d)$$

where $A_1 \in R_+^{m_1 \times n}$, $A_2 \in R_+^{m_2 \times n}$, $A_3 \in R_+^{m_3 \times n}$ are matrices and $b^1 \in R_+^{m_1}$, $b^2 \in R_+^{m_2}$, and $b^3 \in R_+^{m_3}$ are vectors. The subscript + denotes a nonnegative orthant.

The inequalities of System 5a can represent voxels of a first organ at risk (OAR), where an absorbed dose should not exceed $b_t^1$ for each voxel t in the first OAR volume. Examples of OAR volumes include, but are not limited to, brain tissue, muscle tissue, and/or skin tissue. In some embodiments, the inequalities of System 5c can represent voxels of a second organ at risk (OAR), where an absorbed dose should not exceed $b_t^3$ for each voxel t in the second OAR volume. The inequalities of System 5b can represent voxels of a planning target volume (PTV), where an absorbed dose should not exceed $b_t^3$ but should meet or exceed $b_t^2$ for each voxel t in the first OAR volume. Each voxel that does not satisfy the constraints described above can be said to be violating the constraint (e.g., inequality).

In some embodiments, the solver can "translate" integer constraints (e.g., percentage violation constraints $\alpha$, $\beta$) into a "continuous" constraint by taking a sparsity norm, or zero-norm, of a vector $x \in R^n$. In some embodiments, the sparsity norm can be defined as $$\|x\|_0 := |\{x_i | x_i \neq 0\}| \quad (6)$$

where $|\cdot|$ dentes the cardinality (e.g., number of elements) of a set. As described in System 6, the sparsity norm counts the number of nonzero entries of x. The "lower+operation" on a vector $x \in R^n$ means that, for all $I=1, 2, \ldots, n$, $$(x_+)_i := \max(0, x_i) = \begin{cases} x_i, & \text{if } x_i > 0, \\ 0, & \text{if } x_i \le 0 \end{cases}.$$

As defined above, $x_+$ is a nonnegative vector such that $\|x_+\|_0$ represents the number of positive entries of x, defined by $$\|x_+\|_0 := |\{x_i | x_i > 0\}|$$

In some embodiments, a solution to a different problem involving DVCs (e.g., percentage violation constraints) can be defined and solved. Without being limited by theory, the problem can be set up as follows. Let $x^* \in R^n$ be a solution that satisfies the following systems $$0 \le A_1 x \le (1+\beta) b^1 \quad (7a)$$

$$b^3 \ge A_2 x \ge b^2 \quad (7b)$$

$$0 \le A_3 x \le b^4 \quad (7c)$$

$$x \ge 0 \quad (7d)$$

$$\|(A_1 x - b^1)_+\|_0 \le \alpha m_1 \quad (7e)$$

where $A_1$, $A_2$, $A_3$, $b_1$, $b_2$, $b_3$, and $b_4$ are as in Systems 5a-5d and $\alpha \in [0,1]$ and $\beta > 0$.

As described above, System 7a allows the dosage of each voxel as described in System 5a be exceeded by a fraction $\beta$. The System 7e includes a term $(A_1 x - b^1)_+$, which is nonnegative and only has nonzero components that violate System 5a. As such, the zero-norm of $(A_1 x - b^1)_+$ is equal to the number of those violations. System 7e requires that the number of violations does not exceed $\alpha m_1$, where $m_1$ is total number of voxels in the OAR described by 7a.

Split Feasibility Problem

Figure 7E:
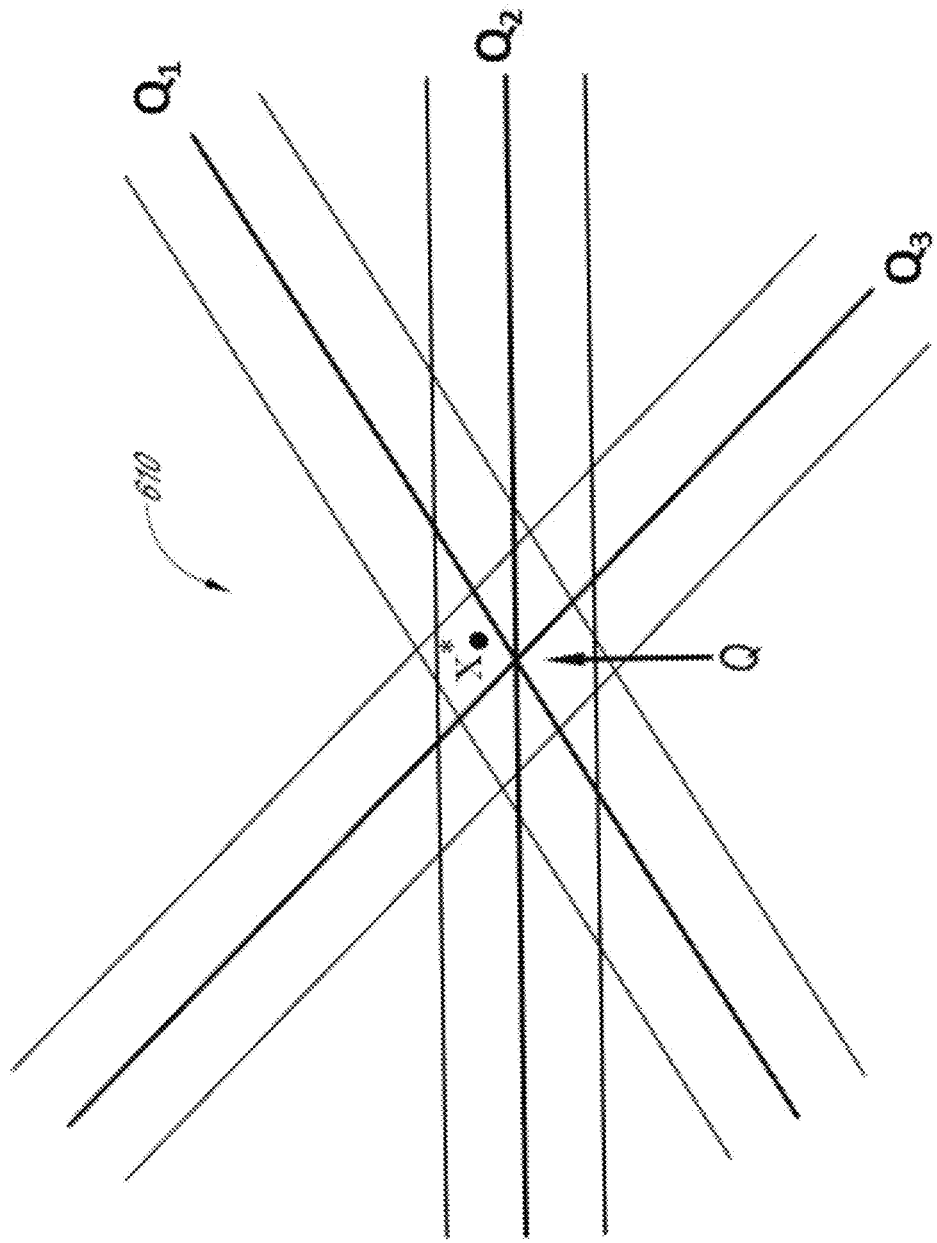
FIG. 7E shows an intersection of hyperplanes.
Figure 8:
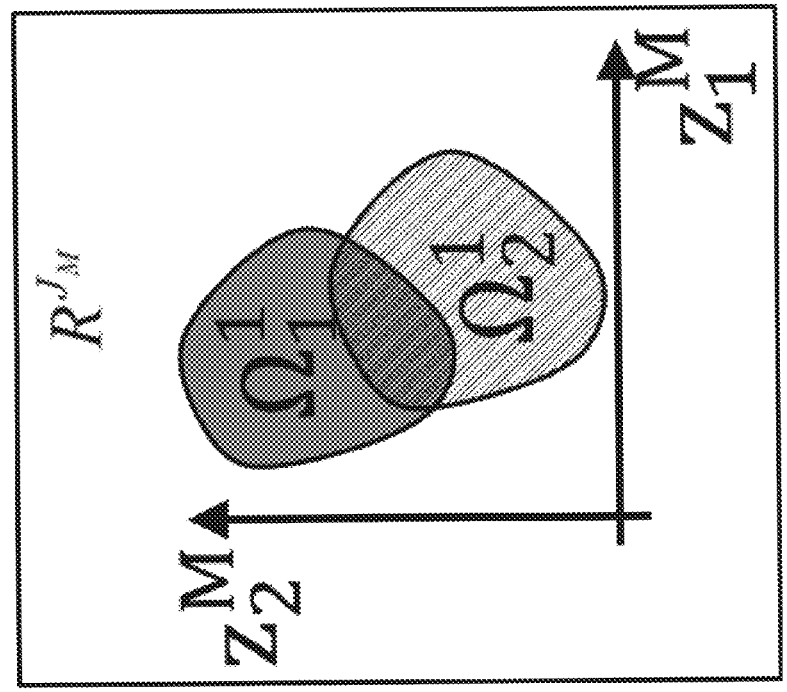
FIG. 8 illustrates the concepts of different spaces.
Figure 8:
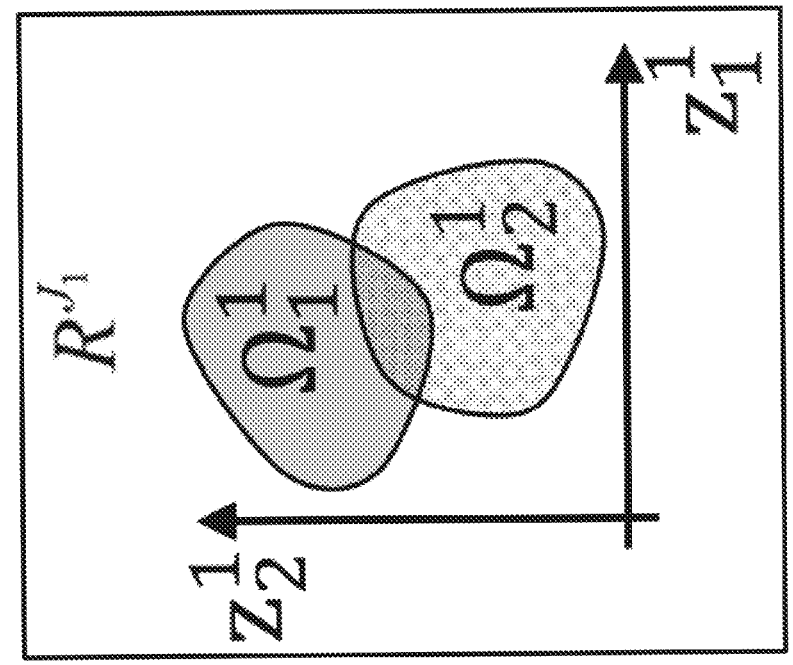
Figure 9:
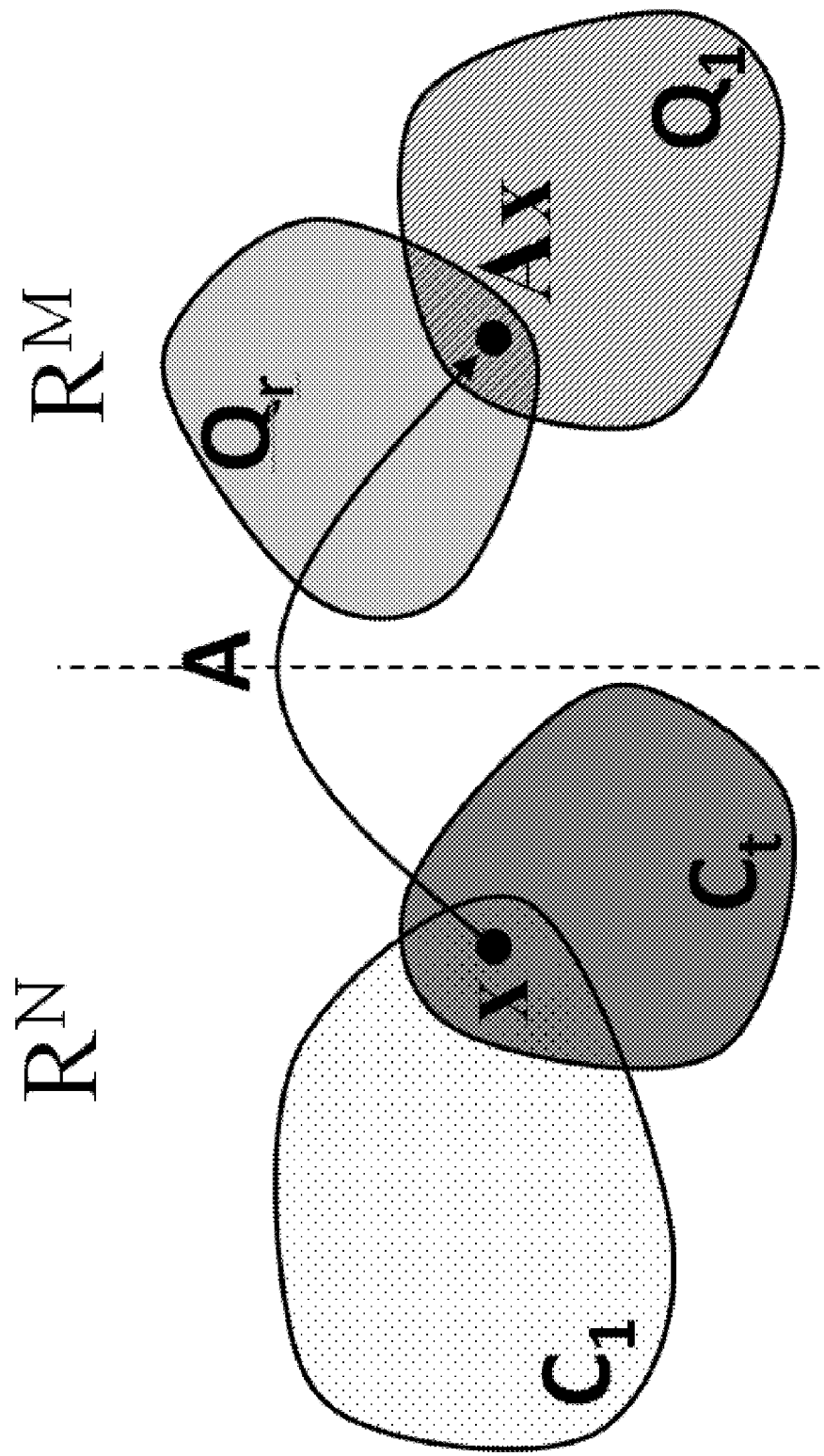
FIG. 9 schematically shows how a projection can be done onto intersecting sets.

A general version of Split Feasibility Problems (SFP) can be described in multiple-sets split feasibility problems (MS SFP). In MS SFP, more than one set exists in both C and in Q. Let sets $C_{1,2...} \in R^N$ and sets $Q_{1,2...} \in R^M$ be closed convex sets. To solve the MS SFP, a solution $x \in C := \cap_{i=1}^t$ must be found such that $Ax \in Q := \cap_{j=1}^T Q_j$ if such an x exists. Constraints $\{Cj\}_{j=1}^J$ can be represented as hyperslabs. In some embodiments, the hyperslabs can lie in a space $R^I$ that describes the pencil beam intensities space. A solution $x^*$ can be represented as lying on the intersection 610 of the hyperslabs $Q_1$, $Q_2$, $Q_3$, as shown in FIG. 7E. In some cases, the solution is an empty set unless additional constraints are included in the system. FIG. 9 shows conceptually the relationship between solutions in spaces $R^N$ to $R^M$. More generally, as shown in FIG. 8, intersections of the sets can have the following relationship: $R^J = R^{J_1} \times R^{J_2} \times \ldots \times R^{J_M}$.

Projection Methods

In some embodiments, projections onto sets as described can be used. Embodiments of IMPT may employ a variety of projection methods. In some embodiments, simultaneous projection methods are used. In such embodiments, a current iterate $x^k$ can be chosen in order to calculate a next iterate $x^{k+1}$. The next iterate can be calculated as follows:

$$\lambda_k = 1 \quad x^{k+1} = x^k + \lambda_k \sum_{i=1}^m w_i (P_i(x^k) - x^k).$$

Figure 7A:
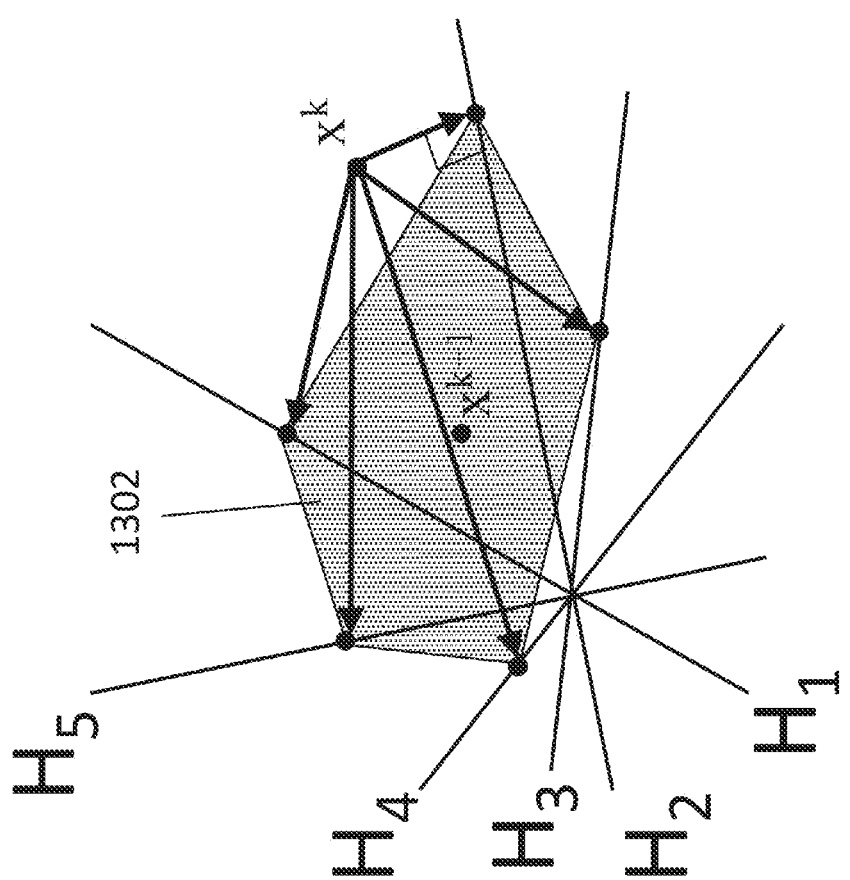
FIGS. 7A-7D show various types of projection algorithms.

FIG. 7A illustrates conceptually how some embodiments of simultaneous projections are performed. As shown in FIG. 7A, the next iterate $x^{k+1}$ can lie in a block 1302 determined by the hyperplanes $H_1$-$H_5$. For each successive iteration calculation, k can be replaced by the stepped value k+1 and the calculation can be repeated. The method can repeat the iteration as often as needed (e.g., until a stopping criterion is met).

In some embodiments of IMPT, sequential projection methods can be used. In some embodiments, sequential successive projections may be used. Examples of sequential successive projections include POCS, ART, Kaczmarz, and Row-Action projection methods, but this should not be read as limiting the types of projections methods that can be used. In some embodiments, the solver can set a current iterate $x^k$ for which the next iterate $$x^{k+1} = x^k + \lambda_k (P_{C_{(k)}}(x^k) - x^k), \lambda_k = 1$$

can be calculated, where $$\langle a^i, x \rangle - b_i = 0, i = 1, 2, \ldots, m$$

and $$x^{k+1} = x^k + \lambda_k \frac{b_{i(k)} - \langle a^{i(k)}, x^k \rangle}{\|a^{i(k)}\|^2} a^{i(k)}$$

Figure 7B:
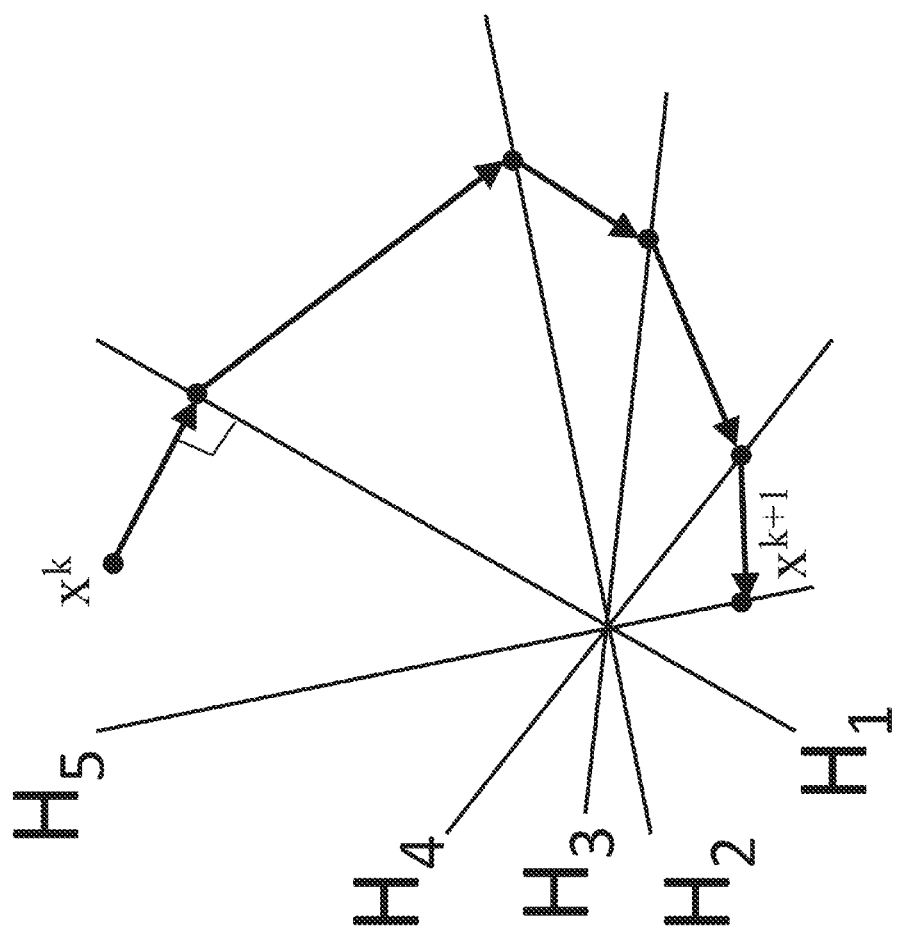

As illustrated by FIG. 7B, iterations can be achieved through individual projections onto successive hyperslabs $H_1$-$H_5$. Because the projections can be done one at a time, sequential methods can require higher processing resources and/or time relative to other projection methods. For each successive iteration calculation, k can be replaced by the stepped value k+1 and the calculation can be repeated. The method can repeat the iteration as often as needed (e.g., until a stopping criterion is met).

Figure 7C:
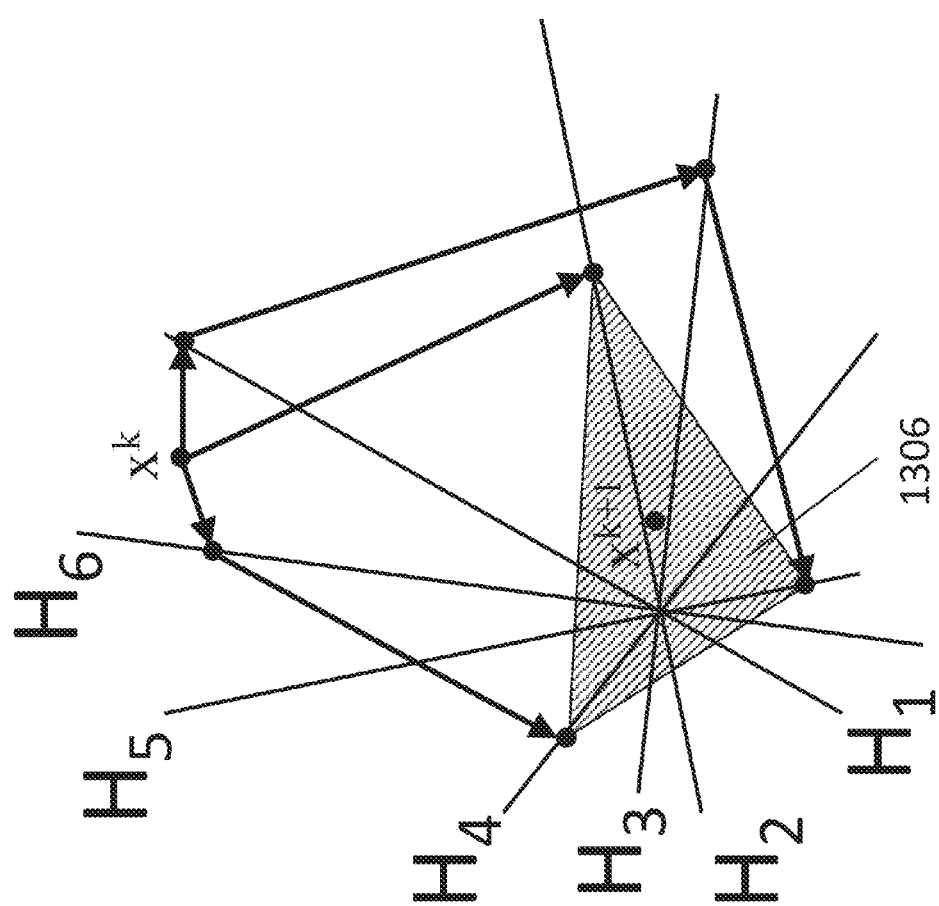

Some embodiments of IMPT can use string averaging projections (SAP). SAP methods can run projections in parallel, thus decreasing computing time. Strings can be assigned for different steps in the projection method. As shown in FIG. 7C, for example, one embodiment set strings $I_1 = (1,2,5,6)$, $I_2 = (2)$, and $I_3 = (6,4)$. The next iterate $x^{k+1}$ can be found on a block defined by a relationship with the resulting string projections. For example, in some embodiments, the string projection can average the resulting projections. For each successive iteration calculation, k can be replaced by the stepped value k+1 and the calculation can be repeated. The method can repeat the iteration as often as needed (e.g., until a stopping criterion is met).

Figure 7D:
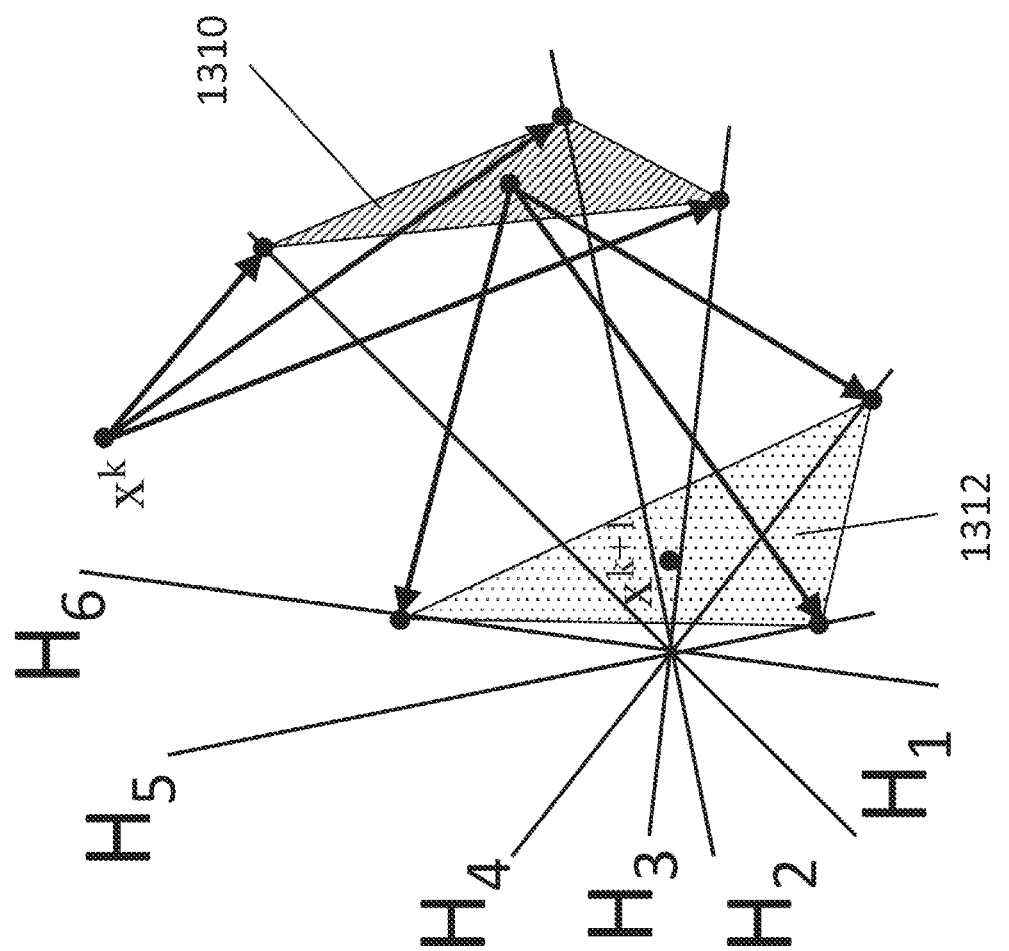

Another parallel projection method that can be used by IMPT are block iterative projections (BIP). In BIP, successive blocks 1310, 1312 can determine the location of a next iterate $x^{k+1}$. As shown in FIG. 7D, a first block 1310 can be determined by a first set of projections. Projections for a second block 1312 can originate from a point from the first block 1310. In some embodiments, the next iterate can lie in an approximate midpoint of the block 1312. For each successive iteration calculation, k can be replaced by the stepped value k+1 and the calculation can be repeated. The method can repeat the iteration as often as needed (e.g., until a stopping criterion is met).

In some embodiments of IMPT, projection methods can be used to solve the linear interval feasibility problem (LIFP). In some embodiments, an Agmon-Motzkin-Schoenberg (AMS) cyclic feasibility-seeking algorithm can be used. Some embodiments employ automatic relaxation methods (ARM). Without being limited by theory, ARM has a benefit of being able to handle each side of inequalities separately. In certain embodiments, ARM can handle inequalities with additional interval constraints. In some embodiments, ARM can automatically and/or continuously determine how close a point is from a hyperslab. ARM can adjust the relaxation parameters as needed.

Some embodiments of ARM can be described as follows. Let large (and possibly sparse) systems of interval linear inequalities take the form $$w_j \leq \langle a^j, x \rangle \leq v_j, j=1, 2, \ldots, p$$

where $a_j \in R^n$ for all j and $w=(w_j) \in R^p$, and $v=(v_j) \in R^p$. In such a case, the system represents p nonempty hyperslabs in $R^n$. In some cases, a problem can be addressed as a system of 2p linear equations solved by the AMS algorithm. In some embodiments of ARM, a specific relaxation principle can be employed in an automatic matter. For each hyperslab of the system above, $$\overline{H}_j := \{x \in R^n | \langle a^j, x \rangle = v_j\} \text{ and } \underline{H}_j := \{x \in R^n | \langle a^j, x \rangle = w_j\}$$

can denote its bounding hyperplanes, where the median hyperplane will be $$H_j := \{x \in R^n | \langle a^j, x \rangle = \frac{1}{2}(v_j + w_j)\}$$

and the half-width $\psi j$ can be given by $$\psi_j = \frac{v_j - w_j}{2\|a^j\|},$$

where $\|\cdot\|$ stands for the Euclidean 2-norm. The signed distance of a point z from the j-th median hyperplane $H_j$ can be given by $$d(z, H_j) = \frac{\langle a^j, z \rangle - \frac{1}{2}(v_j + w_j)}{\|a^j\|}$$

where $$d_{j(k)} := d(x^k, H_{j(k)}).$$

In some embodiments, the solver can initialize an arbitrary $x^0 \in R^n$. It will be appreciated that the terms $R^n$ and $R^N$ (and similar terms) are used interchangeably herein. In some embodiments, a next iterate $x^{k+1}$ can be calculated as follows:

$$x^{k+1} = \begin{cases} x^k, & \text{if } |d_{j(k)}| \leq \psi_{j(k)}, \\ x^k - \frac{\lambda_k}{2} \left( \frac{d_{j(k)}^2 - \psi_{j(k)}^2}{d_{j(k)}} \right) \frac{a^{j(k)}}{\|a^{j(k)}\|}, & \text{otherwise} \end{cases} \quad (8)$$

In some embodiments, a control sequence $\{j(k)\}_{k=0}^{\infty}$ can be cyclic on $\{1, 2, \ldots, m\}$ for which $j(k)=k \mod m+1$, according to which hyperslabs are chosen during iterations. In some embodiments, external relaxation parameters $\{\lambda_k\}_{k=0}^{\infty}$ are confined to $$\epsilon_1 \leq \lambda_k \leq 2 - \epsilon_2, \text{ for some user-chosen } \epsilon_1, \epsilon_2 > 0$$

for all $k \geq 0$. For each successive iteration calculation, k can be replaced by the stepped value k+1 and the calculation can be repeated. The method can repeat the iteration as often as needed (e.g., until a stopping criterion is met).

Superiorization in IMPT

In some implementations, the foregoing projection method that provides an efficient feasibility seeking capability can be selected based on one or more factors that include bounded perturbation resilience. An ability to perturb a given projection algorithm without losing convergence to a feasible point can allow steering of the algorithm toward a feasible point that is superior, in the context of the merit function, than another feasible point that would be arrived at without the perturbations.

Without desiring or intending to be bound by any particular theory, an algorithm P can be said to be resilient to bounded perturbations if the following are satisfied. If a sequence $$((P)^k x)_{k=0}^{\infty}$$

(obtained by sequential repeated applications of P, starting from x) converges to a solution of problem Q for all x in the n-dimensional real coordinate space $R^n$, then any sequence $$(x^k)_{k=0}^{\infty}$$

of points in $R^n$ also converges to a solution of Q provided that for all $k \geq 0$, $$x^{k+1} = P_Q(x^k + \beta_k v^k), \quad (6)$$

where $\beta_k v^k$ are bounded perturbations, meaning that $\beta_k$ are real non-negative numbers such that $$\Sigma_{k=0}^{\infty} \beta_k < \infty$$

and the sequence of vectors $$(v^k)_{k=0}^{\infty}$$

is bounded.

In some implementations, the superiorization methodology can be utilized as follows. Instead of trying to solve a constrained minimization problem, the superiorization approach can perturb some feasibility seeking algorithms so that, without losing their convergence toward feasibility, they will yield a point (or points) with reduced objective function value(s). Thus, in some implementations, one or more feasibility seeking projection algorithms for pCT imaging can include or be adapted to include such a perturbation resilience property. Non-limiting examples of such perturbation resilient projection algorithms, or algorithms that can be adapted to include such a capability, are described herein in greater detail.

Applicant has analyzed a number of projection algorithms that can be utilized for the superiorization methodology; and some results of such analyses are described in reference to FIGS. 21-23. FIGS. 21A and 21B show performance curves (e.g., relative error as a function of number of iteration cycles) for reconstructions of simulated GEANT4 proton interactions using example projection algorithms ART (650), BIP (652), SAP (654), OSART (656), BICAV (658), DROP (660), and CARP (662). FIG. 22 shows an image of a phantom (upper row, first column) that was used in the simulation of the proton interactions, as well as reconstructed images using the foregoing projection algorithms. FIG. 23 shows a comparison of images obtained by different numbers of iterations of an example projection algorithm (DROP), showing that in some situations, additional iterations beyond some point do not necessarily increase the image quality significantly.

The example performance related plots and images of FIGS. 21-23 were obtained using a known optimization technique. Additional references to these example performance related illustrations are made in descriptions of the example projection algorithms.

In some implementations, a perturbation vector v for steering the iterative sequence of image estimates towards reduced total variation of the image estimate can be calculated. For example, the perturbation vector can be calculated as the negative of a normalized subgradient of the total variation at $x^k$, such that $$v^k = \begin{cases} -\dfrac{s^k}{\|s^k\|}, & \text{if } s^k \neq 0, \\ 0, & \text{otherwise} \end{cases} \quad (10)$$

In some implementations, the example subgradient (s) of total variation can be calculated in a manner described in an article authored by P. L. Combettes and J. Luo, "An adaptive level set method for nondifferentiable constrained image recovery," IEEE Trans. Image Process, 11, 1295-1304 (2002). Additional details concerning the foregoing example perturbation vector can be found in, for example, an article authored by D. Butnariu, R. Davidi, G. T. Herman, and I. G. Kazantsev, "Stable convergence behavior under summable perturbations of a class of projection methods for convex feasibility and optimization problems," IEEE J. Sel. Top. Signal Process, 1, 540-547 (2007).

IMPT with Dose Volume Constraints

In implementations where the CFP is inconsistent (e.g., when Q=Ø), a solution can be found by solving a linear feasibility problem (LFP) and assigning percentage violation constraints (PVC).

Some embodiments can allow a user to set one or more constraints on the IMPT to achieve the desired dosages. In some cases, such a constraint may refer to a dose-volume constraint (DVC). As used herein, a DVC may refer to a dose limit such that other DVCs are calculated based on the dose limit. In some cases, a DVC can describe the limit of radiation that is desired by a treatment planner or physician. For example, a physician may prescribe an upper and lower limit of a desired dosage.

In some embodiments, a DVC may describe a limit to which a dosage limit can be violated. A physician may set a DVC such that up to a maximum fraction of a target volume (e.g., organ volume) may violate a limit by up to a maximum value. Such a bound may be, for example, an upper bound limit or a lower bound limit. In some cases, the physician or treatment planner may choose a first DVC $\alpha$ and/or a second DVC $\beta$ such that a fraction $\alpha$ of the target volume will not receive more than a $\beta$ amount of radiation. In some cases the amount $\beta$ may be given as a fraction of an integer and/or as a total number of units of radiation (e.g., Grays). In some embodiments, $\alpha$ and $\beta$ may be referred to as percentage-violation constraints (PVC).

In some embodiments, a vector $x^*$ can be found that solves the system $$\begin{cases} (i) \langle a^j, x \rangle \leq (1+\beta) u_j, \text{ for all } j \in B, \\ (ii) h(x) \leq \alpha \beta |B| \end{cases} \quad (9)$$

where the function $h: R^I \to R$ is a defined function of the vector x that is convex in x and whose subgradients or gradients are easily calculated.

Without being limited by theory, it is believed that once a vector $x^*$ is found that satisfies System 9, $x^*$ can be used to solve the dose-volume constraints feasibility problem of certain embodiments. In these embodiments, a finite index set B, vectors $\{a^j\}_{j \in B}$, upper bounds $u_j$ on doses to voxels for all $j \in B$, and $\alpha$ and $\beta$ can be set such that $0 \leq \alpha \leq 1$ and $0 \leq \beta < 1$.

In addition to these settings, if percentage violation constraints (PVC) are set such that in up to a fraction $\alpha$ of the inequalities $$\langle a^j, x \rangle \leq u_j \text{ for all } j \in B \quad (10)$$

may be violated by up to a fraction $\beta$, the vector $x^*$ will satisfy system 9.

In some embodiments, the LFP can be solved by finding a vector $x^*$ that satisfies certain conditions. In embodiments where Q=Ø, $x^*$ can be determined if a PVC also applies such that in up to a fraction of the total number of inequalities $$\langle a^j, x \rangle \leq v_j, \text{ for all } j \in J \quad (11)$$

the right-hand side bounds $v_j$ may be potentially violated by up to a fraction of their values. One condition can include that $x^*$ solve the system.

The constraints described in Systems 7a-7c can be described by $c \leq Ax \leq b$, where A is an $(m_1+m_2+m_3) \times n$ matrix composed of blocks $$A := \begin{pmatrix} A_1 \\ A_2 \\ A_3 \end{pmatrix}$$

And b and c are each $(m_1+m_2+m_3)$ vectors given, respectively, by $$b := \begin{pmatrix} (1+\beta)b^1 \\ b^3 \\ b^4 \end{pmatrix}$$

$$c := \begin{pmatrix} 0 \\ b^2 \\ 0 \end{pmatrix}$$

Because each of A, b, and c reside in the space Rn, the space of intensity vectors x, and because the sparsity constraint takes place in the space Rm1, the space of OAR dose vectors, a method for seeking feasible solutions of split feasibility problem (SFP) can be used.

In some embodiments, the solver can define C in the same space $R^n$ as the intensity vectors x, such that $$C := \{x \in R^n | c \leq Ax \leq b\} \cap R_+^n$$

and Q in the same space $R^{m1}$ as the OAR dose vectors, such that $$Q := \{y \in R^{m1} | \|(y-b^1)_+\|_0 \leq \alpha m_1\}.$$

In some embodiments, a solution $x^* \in C$ can be found such that $A_1 x^* \in Q$. In some cases, Q is not a convex set. In certain embodiments, the solver can project onto Q orthogonally using a feasibility-seeking projection method.

In some embodiments, a projected Landweber method can be used. In certain embodiments, the projected Landweber method comprises using a CQ-algorithm. Certain embodiments of the CQ-algorithm do not require the calculation of the inverse $A_1^{-1}$ of $A_1$. Such embodiments may need to calculate $A_1^T$ instead. An algorithm $P_\Omega(z)$ can project a vector z orthogonally onto a set $\Omega$. In certain embodiments, because Q is not convex, a next iterate $x^{k+1}$ may comprise more than one point for $P_Q$. In such embodiments, the point may be chosen arbitrarily.

In some embodiments, the CQ algorithm can include setting an arbitrary $x^0 \in R^n$ and k=0. The CQ algorithm can further include calculating a next iterate xk+1 using $$x^{k+1} = P_C(x^k + \gamma A_1^T (P_Q(A_1 x^k) - A_1 x^k)) \quad (12)$$

For each successive iteration calculation, k can be replaced by the stepped value k+1 and the calculation can be repeated. The method can repeat the iteration as often as needed (e.g., until a stopping criterion is met).

A $P_Q(z)$ can be calculated such that $$P_Q(z) = P_{\overline{Q}}(z - b^1) + b^1$$

where $$\overline{Q} := \{y \in R^{m_1} | \|y_+\|_0 \le \alpha m_1\}.$$

As described the solver can project a shifted point $(z-b^1)$ onto the set $\overline{Q}$ and adding b1 in order to project a point z onto the set Q. Thus, a projection onto $\overline{Q}$ should be calculated. In some embodiments, the number l of positive components of $(z-b^1)$ can be described by the relationship in an algorithm $$P_{\overline{Q}}(z - b^1) = \begin{cases} (z - b^1), & \text{If } l \le \alpha m_1 \\ w, & \text{If } l > \alpha m_1 \end{cases} \quad (13)$$

where w is the vector obtained from $(z-b^1)$ by replacing its smallest positive $l-\alpha m_1$ components with zeros. At this point, if $l \le \alpha m_1$, then the point $(z-b^1)$ is on $\overline{Q}$ and $P_{\overline{Q}}(z-b^1) = (z-b^1)$. This result can be used for $z = A_1 x^k$ in System 5a.

In some embodiments a parameter $\gamma$ can be chosen. In certain embodiments, the parameter $\gamma$ is found on the interval $0 < \gamma < 2/\theta$. In IMPT, some embodiments permit the parameter $\gamma$ to be set by a user (e.g., doctor, treatment planner, etc.).

In some embodiments, $\theta$ can defined as $$\theta := \|A_1\|_F^2 = \sum_{i=1}^{m_1} \sum_{j=1}^{n} |a_{ij}|^2$$

using the squared Frobenius matrix norm $\|A_1\|_F^2$, where i=1, 2, ..., $m_1$ and j=1, 2, ..., n.

In certain embodiments, the solver can employ a dose-volume split-feasibility (DVSF) algorithm. In some embodiments, the DVSF algorithm can include calculating the transposed matrix $A_1^T$, the value of $\theta$, and choosing a parameter $\gamma$, as described here. In some embodiments, the algorithm includes taking an arbitrary $x^0 \in R^n$ and setting k=0. The algorithm can further include projecting $A_1 x^k$ onto Q. In some embodiments, projecting $A_1 x^k$ onto Q can include computing $A_1 x^k$ for the current iterate $x^k$ and counting the positive coordinates of $(A_1 x^k - b^1)$. In some embodiments, the positive coordinates can be denoted by l. A further step in the algorithm can include calculating $$v^k := P_{\overline{Q}}(A_1 x^k - b^1)$$

using Equation 13 where $z = A_1 x^k$. In some embodiments, the solver can calculate a projection $A_1 x^k$ onto Q using $$P_Q(A_1 x^k) = v^k + b^1$$

in the algorithm. In some embodiments, the algorithm can calculated, for $u^k \in R^n$, using $$u^k = x^k + \gamma A_1^T (P_Q(A_1 x^k) - A_1 x^k)$$

In some embodiments, a projection of $u^k$ onto C can be done using Equation 12. In some configurations, the solver can perform one or more sweeps of a feasibility-seeking projection method for Systems 5a-5d. In some embodiments, for each sweep, k can be replaced by the stepped value k+1 and the calculations in Systems 5a-5d can be repeated. The sweeps can repeat the iteration as often as needed (e.g., until a stopping criterion is met). In some embodiments, the sweeps can include obtaining multiple values of $u^k$ using Systems. In certain embodiments, when the sweeps have stopped, the resulting vector can be used as the next iterate $x^{k+1}$ in Equation 12.

In some embodiments, for each successive iteration calculation, k can be replaced by the stepped value k+1 and the DVSF algorithm can be repeated. The algorithm can repeat as often as needed (e.g., until a stopping criterion is met).

As described herein, the methods and systems described herein may apply to particle as well as electromagnetic (e.g., gamma ray) radiation. In some embodiments, the IMPT uses gamma rays. In some embodiments, the radiation is comprised of particles (e.g., ions). In certain embodiments, the particles consist of protons and/or carbon ions.

Figure 10:
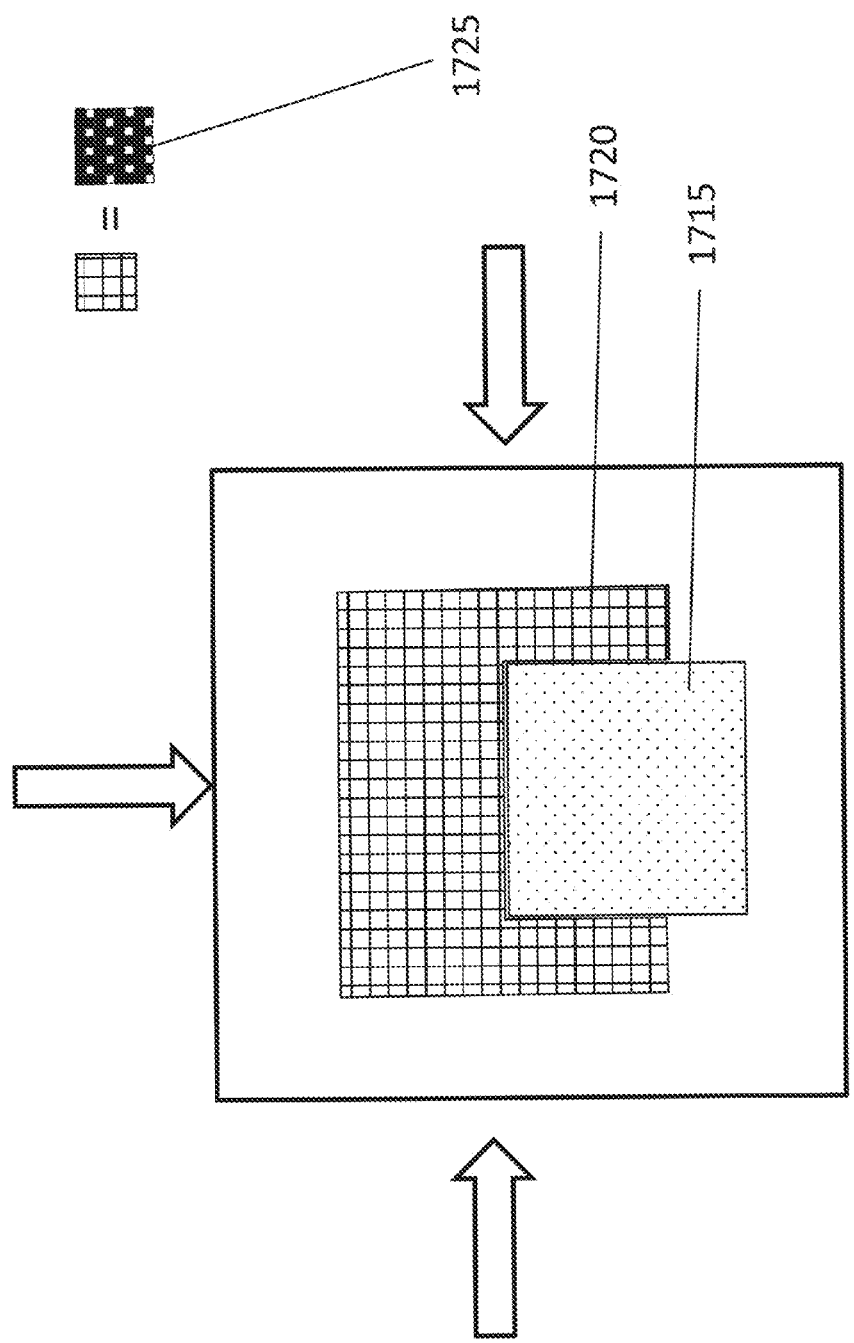
FIG. 10 shows a schematic of how target volumes can be arranged.

In some embodiments one or more particle beams and/or angles can be used. FIG. 10 shows a schematic of dosage regions. For example, a first region 1715 can refer to an organ at risk (OAR). A second region 1720 can represent a planning target volume (PTV) (e.g., a tumor). As shown in FIG. 10, in some embodiments three particle beams are used (as indicated by the arrows). However, this should not be viewed as limiting, as one, two, or more than three beams may be used. Similarly, one or more beam angles may be used.

In certain embodiments, the number of beamlets in each beam can vary. For example, in one embodiment, 146 particle beamlets were used per beam, but the number of beamlets can range from about 30-230 beamlets. In some embodiments, the number of beamlets in each beam can be higher, such as between about 350-780 beamlets. In some embodiments, the amount of dose deposited by each pencil beamlet can be calculated with a Monte Carlo toolkit Geant4 and/or recorded.

The beam diameter can range from about 0.5-4 mm diameter. As an example, a beamlet can be about 2 mm in one embodiment. The spacing of the pencil beamlets in different embodiments can range from about 1-3 mm in diameter. In some embodiments, the spacing is about 2 mm. As shown in FIG. 10, in some embodiments Bragg peaks can be delivered in a pattern similar to the pattern 1725, where, for example, white dots represent where Bragg peaks were delivered. Beamlet energies in some embodiments can range from about 95 MeV-175 MeV. In certain embodiments, the energies can range from about 75 MeV-200 MeV. The resolution can be approximately 0.5 MeV, such as a range of about 0.1-0.9 MeV. In some cases, it may be assumed that the structures of the irradiated area approximate the characteristics of water.

In some embodiments of the IMPT system, a pre-absorber can be inserted into the beams in front of the irradiated geometry at a distance from the irradiated structures. In some embodiments, this distance can be between about 3 and 8 cm. In some embodiments, the pre-absorber can comprise polyethylene. In certain configurations, the thickness of the pre-absorber can be between about 2 and 10 cm.

In certain configurations of modeling of physical phenomena, particles and/or electromagnetic waves may be tracked using standard electromagnetic physics (e.g., G4EmStandardPhysics) and/or hadron physics models (e.g., G4HadronPhysicsQGSP_BIC_HP).

As described herein, certain embodiments included dose only constraints (DOCs). In some embodiments, a single dose volume constraint (DVC) is applied. In some embodiments, two or more DVCs can be used. The DOCs and/or DVCs may be applied to PTV and/or OAR volumes. Table 1 shows a list of sample DVCs that may be used in treatment in various embodiments of IMPT. As used in Table 1, a dose volume constraint (e.g., percentage violation constraint) combination such as $\alpha=0.2$, $b_1=40$ Gy, and $\beta=0.25$ would correspond to $D_{20\%} \leq 40$ Gy and $D_{max}=50$ Gy.

Figures 11A, 11B, 11C:
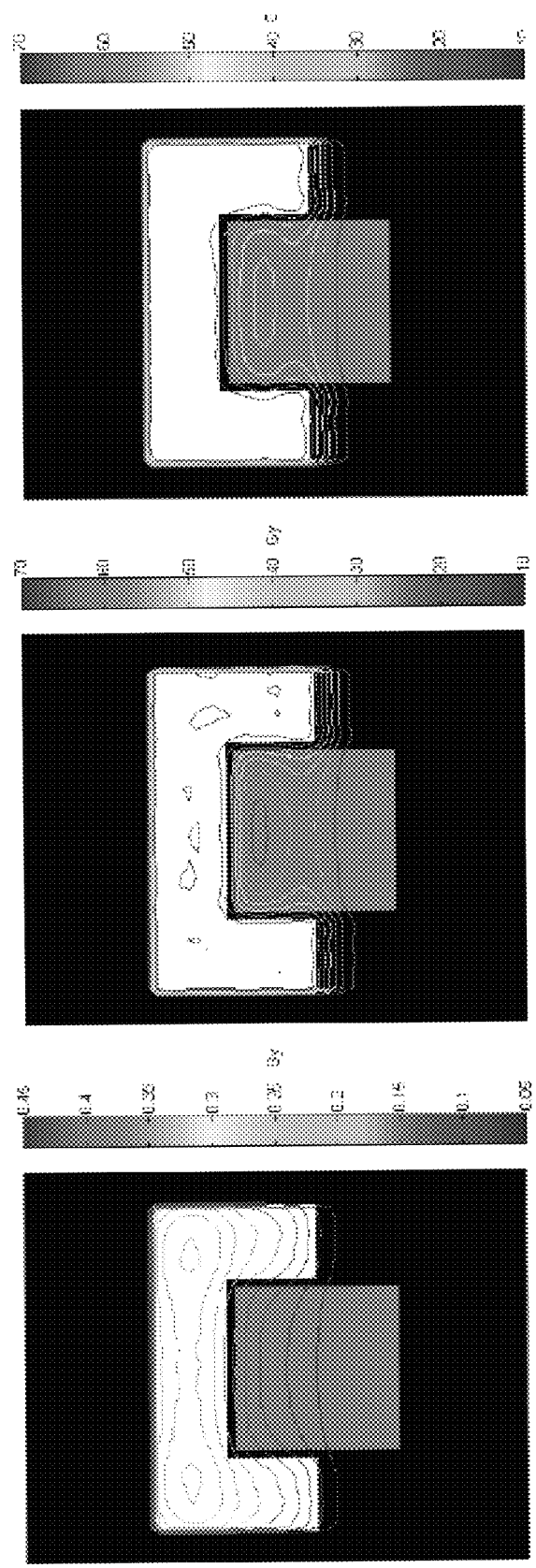
FIGS. 11A-C show results from several embodiments of IMPT.
Figure 12A:
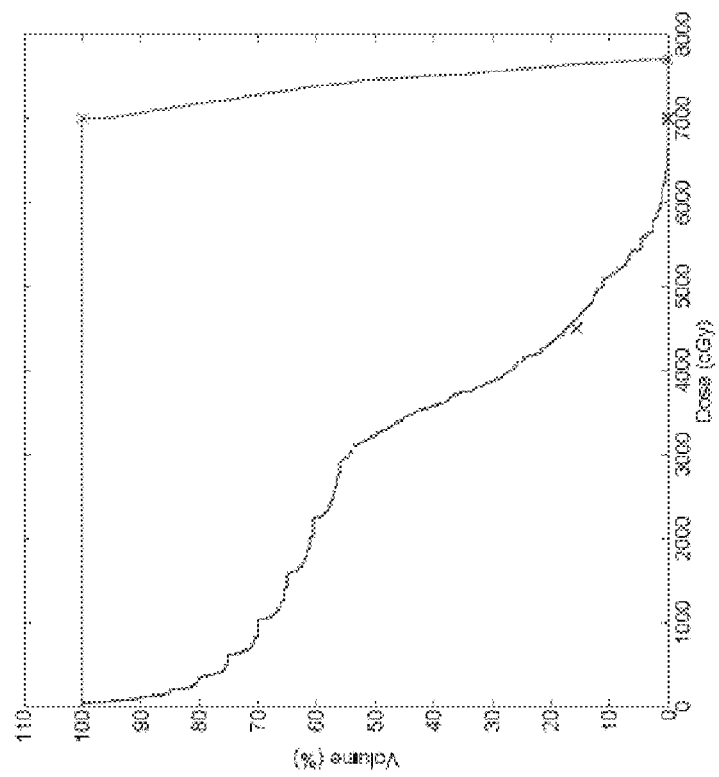
FIGS. 12A-D show results from several embodiments of IMPT.
Figure 12B:
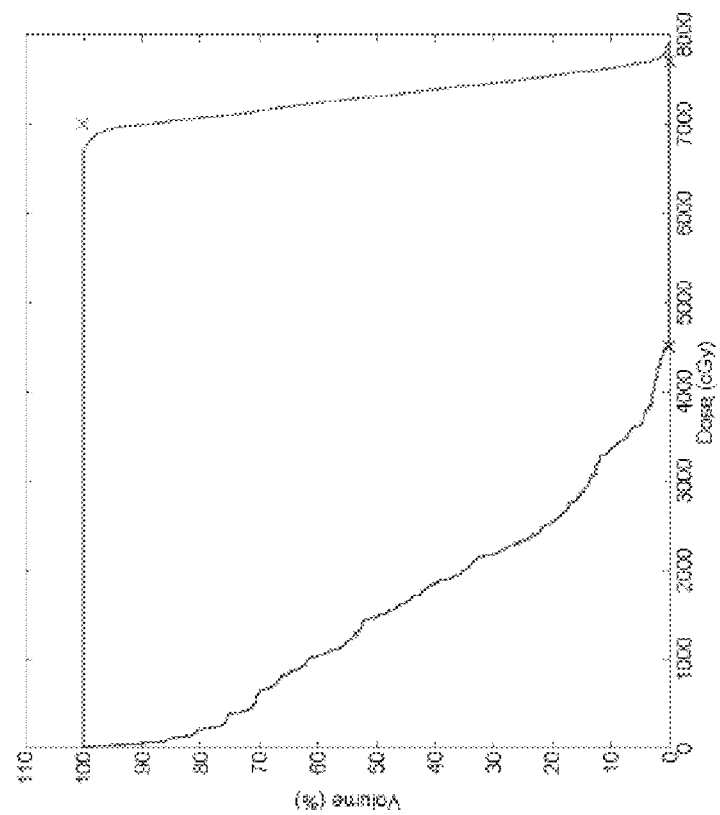
Figure 12C:
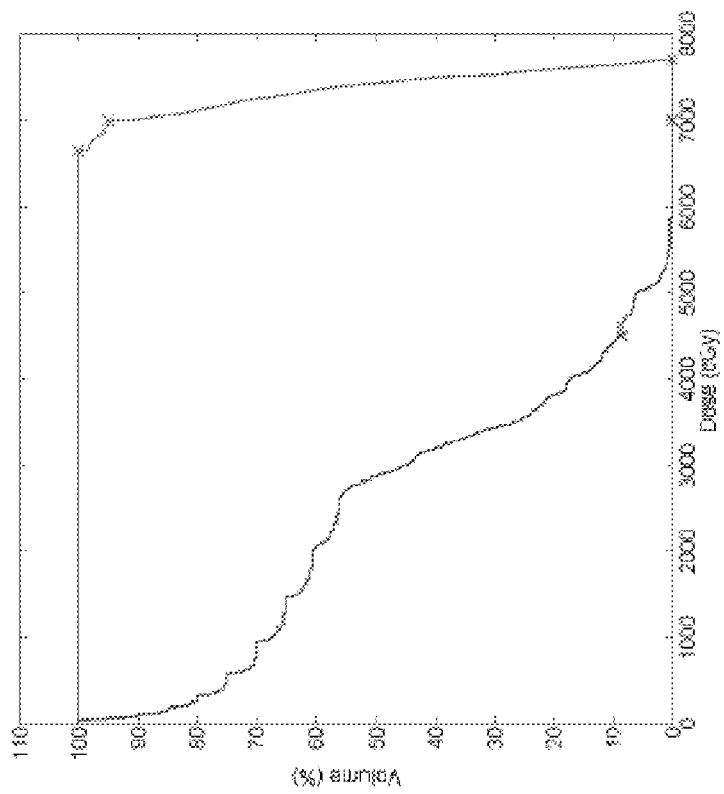
Figure 12D:
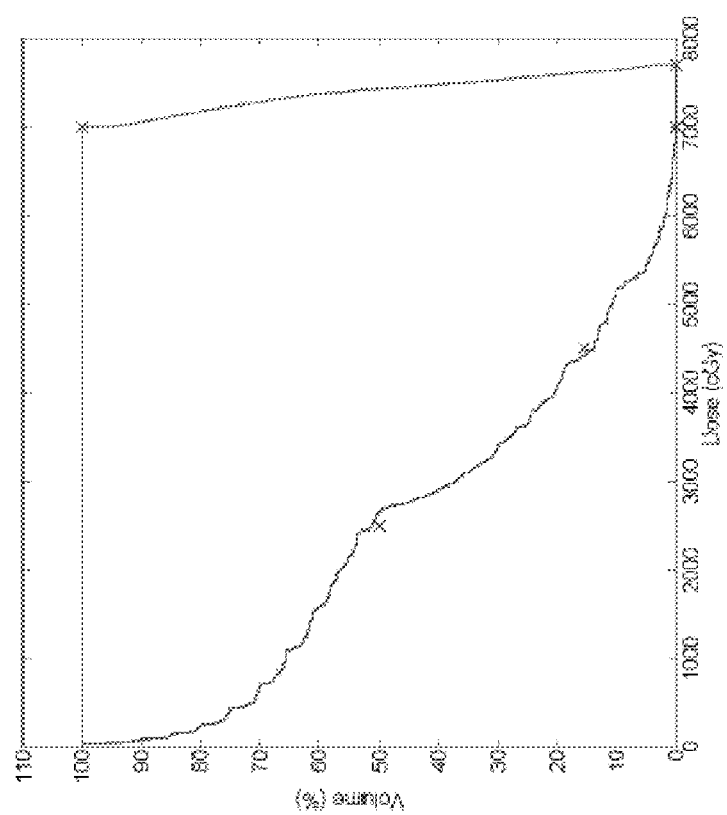

FIGS. 11A-C depict isodose contours. FIG. 11A shows the results of unit intensity pencil beams. FIG. 11B shows the results of DOCs, corresponding to Prescription 1 of Table 1. FIG. 11C shows the results of DVCs applied to both PTV and OAR structures, corresponding to Prescription 4.

FIGS. 12A-D represent histograms simulated results of each of the prescriptions tested from Table 1. In each histogram, the upper curve represents the PTV and the lower curve represents the OAR. DVCs are indicated by small crosses. FIGS. 3A-D corresponds to Prescriptions 1-4, respectively.

In some embodiments, an initial pencil beam intensity vector can range from about 0.3 to 1.8 units. Certain embodiments of the IMPT method and/or system can cycle through the algorithms described herein one or more times. In some embodiments, the number of cycles can be between 1200-3200 cycles. In some embodiments, the number of cycles is fewer in order to conserve computation power and/or time. In such cases, the number of cycles can range from about 100-1400 cycles. As used herein, cycle can refer to one complete processing of all DVCs and/or DOCs applied to each pixel within the PTV and/or the OAR structures.

Some embodiments can run MATLAB (The MathWorks, Inc.) or some other computation software in order to handle the large numbers involved. In some embodiments the number of voxels along a particular axis (e.g., x, y, or z) of the PTV and/or OAR can range from about 12-120 voxels per axis. For each axis, in some embodiments, the resolution can be between about 0.5-5 mm. Dose grids can be larger, such as up to 4 times as large as the CT pixel size in various embodiments.

In one embodiment, a treatment plan for proton pencil beam scanning (PBS) was developed. Two proton pencil beams targeted the PTV from angles of 80° and 280°, each containing 574 and 564 beamlets, respectively. Parameters were set to have 80% layer overlap, a lateral spot resolution of 0.6 cm, a lateral target margin of 0.4 cm and 3 standard deviation dose spread during dose calculation. The DVCs used are shown in Table 2.

Figures 13A, 13B:
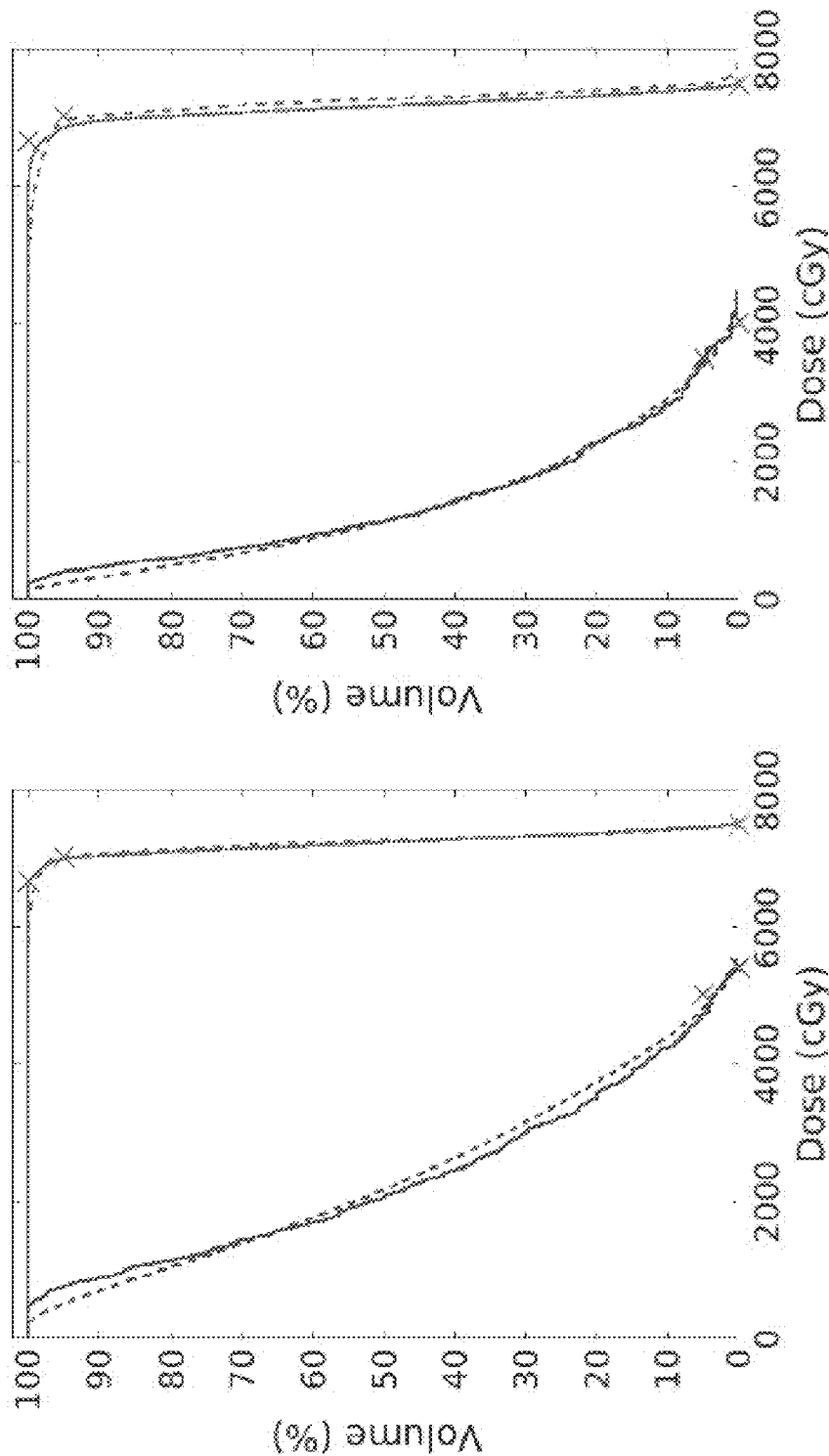
FIGS. 13A-B show results of a clinical test patient in one embodiment of IMPT.

FIG. 13A-B represent test results in a clinical patient. FIG. 13A shows the results when Prescription 1 of Table 2 was applied subject to the following inputs (representing the solid line): Dose-volume histogram (DVH) after 2000 cycles of the DVSF algorithm, using $\gamma_{PTV}=1.99/\theta_{PTV}$, $\gamma_{OAR}=1/\theta_{OAR}$, $\gamma_{PTV}=\gamma_{OAR}$, =1. The dotted line represents a DVH produced by Pinnacle[3] after 86 iterations and meeting a stopping tolerance of less than $10^{-7}$. FIG. 13B shows the results when Prescription 2 was applied subject to the following inputs (representing the solid line): Dose-volume histogram (DVH) after 2000 cycles of the DVSF algorithm, using $\gamma_{PTV}=1.99/\theta_{PTV}$, $\gamma_{OAR}=0.3/\theta_{OAR}$, $\gamma_{PTV}=\gamma_{OAR}$, =0.5. The dotted line represents a DVH produced by Pinnacle[3] after 131 iterations and meeting a stopping tolerance of less than $10^{-7}$.

Figure 14A:
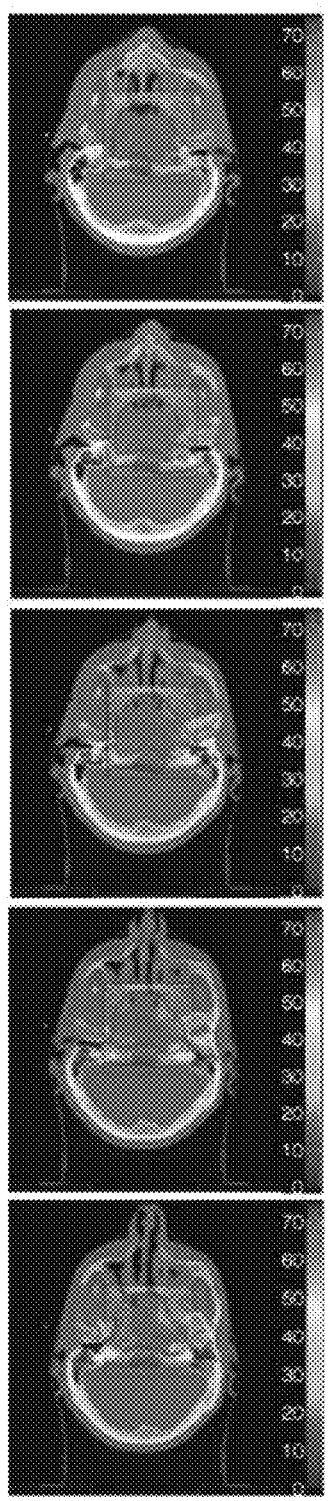
FIGS. 14A-15B show contour maps for various prescriptions of dose volume constraints in some embodiments.
Figure 14B:
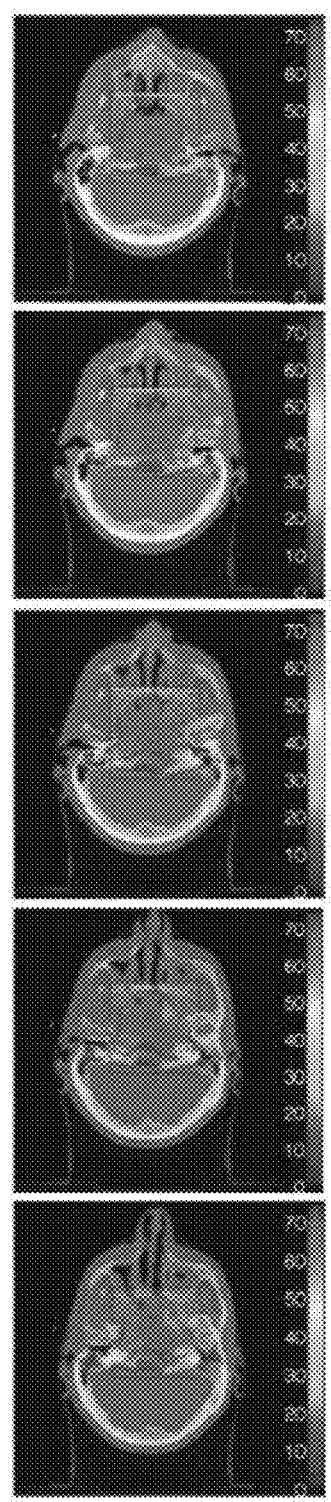

FIGS. 14A-B illustrate dose contour maps when Prescription 1 of Table 2 are applied under different inputs. In FIG. 14A, the inputs are as follows: 2000 cycles of the DVSF algorithm, using $\gamma_{PTV}=1.99/\theta_{PTV}$, $\gamma_{OAR}=1/\theta_{OAR}$, $\gamma_{PTV}=\gamma_{OAR}$,=1. FIG. 14B is produced by Pinnacle[3] after 86 iterations and meeting a stopping tolerance of less than $10^{-7}$. The units of the scales next to each DVH are in Gy.

TABLE 1

Prescriptions associated with PTV and OAR structures in order to test the functionality of the proposed DVSF algorithm (Algorithm 5) in a simplified 2D geometry.

| Prescription | OAR | PTV |
|---|---|---|
| 1 | $D_{max}$ = 45 Gy | $D_{min}$ = 70 Gy |
|   |   | $D_{max}$ = 77 Gy |
| 2 | $D_{15.5\%} \leq 45$ Gy | $D_{min}$ = 70 Gy |
|   | $D_{max}$ = 70 Gy | $D_{max}$ = 77 Gy |
| 3 | $D_{80\%} \leq 25$ Gy | $D_{min}$ = 70 Gy |
|   | $D_{15.5\%} \leq 45$ Gy | $D_{max}$ = 77 Gy |
|   | $D_{max}$ = 70 Gy |   |
| 4 | $D_{8.5\%} \leq 45$ Gy | $D_{min}$ = 66.5 Gy |
|   | $D_{max}$ = 70 Gy | $D_{95\%} \geq 70$ Gy |
|   |   | $D_{max}$ = 77 Gy |

TABLE 2

Prescriptions associated with PTV and OAR (brainstem) structure for a clinical test case.

| Prescription | OAR | PTV |
|---|---|---|
| 1 | $D_{max}$ = 54 Gy | $D_{min}$ = 66.5 Gy |
|   | $D_{5\%} \leq 50$ Gy | $D_{max}$ = 74.9 Gy |
|   |   | $D_{95\%} \geq 70$ Gy |
| 2 | $D_{max}$ = 40 Gy | $D_{min}$ = 66.5 Gy |
|   | $D_{5\%} \leq 35$ Gy | $D_{max}$ = 74.9 Gy |
|   |   | $D_{95\%} \geq 70$ Gy |

Figure 15B:
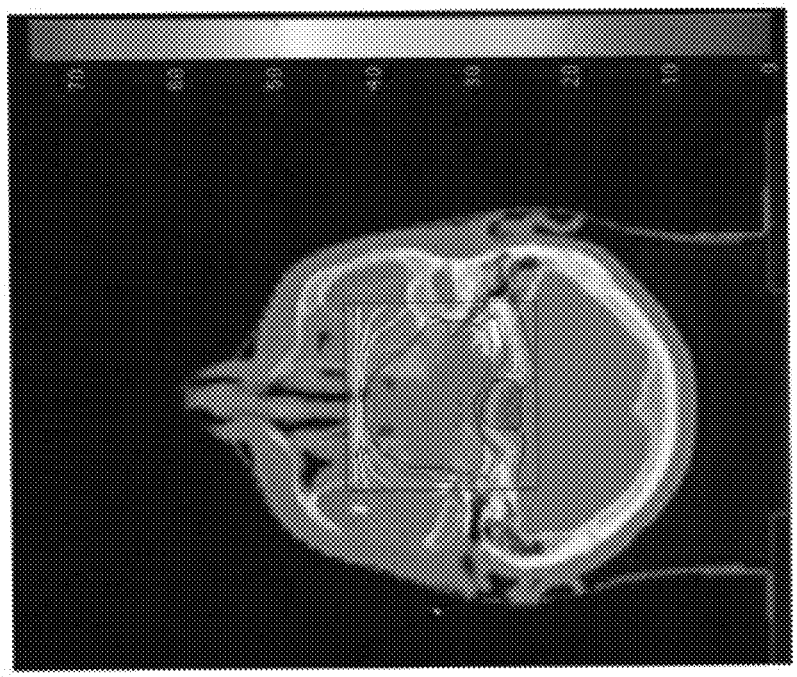
Figure 15A:
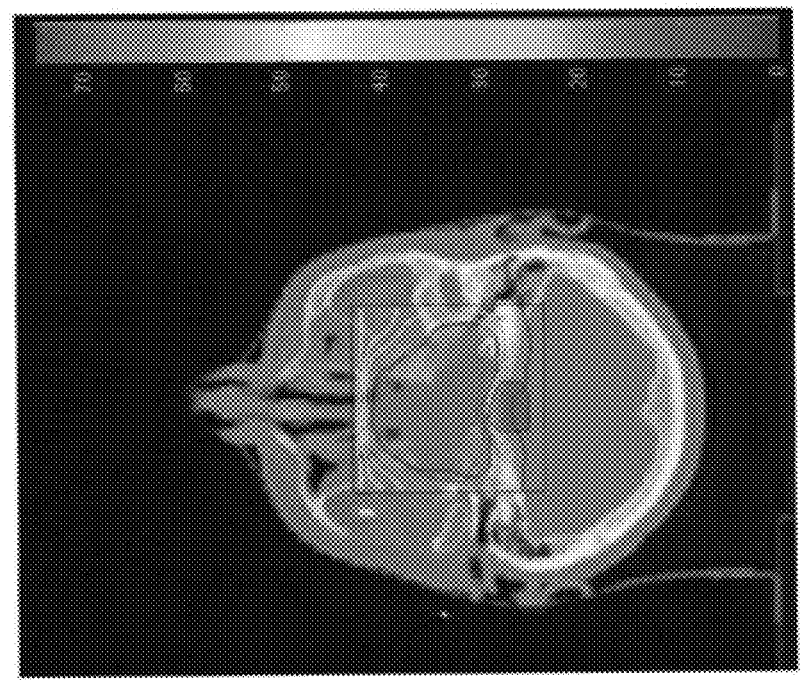

FIGS. 15A-B illustrate dose contour maps when Prescription 2 of Table 2 are applied under different inputs. In FIG. 15A, the inputs are as follows: 2000 cycles of the DVSF algorithm, using $\gamma_{PTV}=1.99/\theta_{PTV}$, $\gamma_{OAR}=0.3/\theta_{OAR}$, $\gamma_{PTV}=\gamma_{OAR}$, =0.5. FIG. 15B is produced by Pinnacle[3] after 131 iterations and meeting a stopping tolerance of less than $10^{-7}$. The units of the scales next to each DVH are in Gy.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment. Accordingly, no feature or group of features is necessary or indispensable to each embodiment.

Embodiments of the disclosed systems and methods may be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprise programmable units, such as programmable gate arrays, application specific integrated circuits, and/or processors. The modules described herein may be implemented as software modules, or may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of non-transitory computer-readable medium or other non-transitory computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

A number of applications, publications, and external documents may be incorporated by reference herein. Any conflict or contradiction between a statement in the body text of this specification and a statement in any of the incorporated documents is to be resolved in favor of the statement in the body text.

Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

The following is claimed:

1. A method for performing intensity-modulated radiation therapy on a subject using a plurality of pencil beams, the method comprising:
    identifying a volume of interest from a representation of the subject, the volume of interest divided into a total number of voxels;
    defining a plurality of sub-volumes, wherein a sub-volume comprises a number of contiguous, ordered voxels; and
    generating a treatment plan for intensity-modulated radiation therapy that satisfies dose constraints for each voxel within each of the plurality of sub-volumes;
    wherein generating the treatment plan comprises:
        determining a system of linear equations of the form $Ax^* = b$ or linear inequalities of the form $b^{min} \leq Ax^* \leq b^{max}$ where $x^*$ is a first vector comprising elements $x_i$ representing an $i^{th}$ component of a solution vector representing an actual intensity of an $i^{th}$ pencil beam, b is a second vector comprising elements $b_j$ representing a dose prescribed for a $j^{th}$ dose grid point, $b^{min}$ is a third vector comprising elements $b^{min}_j$ representing a minimum dose prescribed for a $j^{th}$ dose grid point, $b^{max}$ is a fourth vector comprising elements $b^{max}_j$ representing a maximum dose prescribed for a $j^{th}$ dose grid point, and A is a matrix comprising elements $a_{ij}$ representing a dose delivered by the $i^{th}$ pencil beam of unit intensity to the $j^{th}$ dose grid point; and
        determining one or more feasible solutions $x^*$ to the system of equations or inequalities using a feasibility-seeking algorithm.

2. The method of claim 1, wherein determining one or more feasible solutions $x^*$ comprises, for each of the plurality of sub-volumes, receiving a threshold number of dose constraints that are allowed to be violated when performing intensity-modulated radiation therapy using the one or more feasible solutions $x^*$.

3. The method of claim 1, wherein determining one or more feasible solutions $x^*$ comprises, for each of the plurality of sub-volumes, providing a threshold proportion of dose constraints that are allowed to be violated when performing intensity-modulated radiation therapy using the one or more feasible solutions $x^*$.

4. The method of claim 1, wherein determining one or more feasible solutions $x^*$ comprises performing repeated projections of iterates of preliminary solution vectors onto convex sets determined by the linear system of equations or inequalities.

5. The method of claim 1, wherein determining one or more feasible solutions $x^*$ comprises defining a cost function or optimization function and determining a gradient of the cost function or optimization function in order to find a local minimum.

6. The method of claim 1, wherein generating the treatment plan further comprises perturbing the one or more feasible solutions $x^*$ to determine a perturbed solution superior to a non-perturbed solution, wherein perturbing the one or more feasible solutions comprises adding a perturbation term to the one or more feasible solutions x* that reduces total variation in dose space.

7. The method of claim 6, wherein perturbing the one or more feasible solutions comprises adding a perturbation term repeatedly a specified number of times.

8. The method of claim 6, wherein perturbing the one or more feasible solutions comprises adding a perturbation term repeatedly until a stopping criterion is met.

9. The method of claim 1, wherein satisfying dose constraints for each voxel within each of the plurality of sub-volumes comprises receiving a first violation constraint, wherein the first violation constraint specifies that no more than a fraction of the total number of voxels in the volume of interest are permitted to receive a dose of radiation greater than a maximum dose constraint or less than a minimum dose constraint.

10. The method of claim 9, wherein the minimum dose constraint is a scalar value multiplied by the third vector.

11. The method of claim 9, wherein the maximum dose constraint is zero multiplied by the fourth vector.

12. The method of claim 9, wherein the maximum dose constraint is a scalar value greater than zero multiplied by the fourth vector.

13. The method of claim 1, wherein generating the treatment plan comprises determining whether adding a perturbation term yields a solution that is superior to the estimated initial solution.

14. The method of claim 1, wherein generating the treatment plan comprises the step of determining whether adding a perturbation term yields a solution that reduces total variation in dose space relative to the estimated initial solution.

15. The method of claim 1, wherein generating the treatment plan comprises determining a dose of radiation from the solution vector x*, the dose of radiation comprising one or more of x-rays, electrons, protons, or ions heavier than protons.

16. A method for performing intensity-modulated radiation therapy, the method comprising:
   obtaining a representation of a patient, the representation comprising information about structures within or on the patient;
   identifying a target volume in the representation of the patient;
   identifying an organ at risk or other non-targeted tissue in the representation of the patient;
   dividing the target volume into a first plurality of sub-volumes, wherein dividing the target volume into a first plurality of sub-volumes comprises:
      dividing the target volume into a total number of voxels;
      selecting a first fractional value corresponding to a ratio of a size of a sub-volume of the target volume to a size of the target volume; and
      for each of the first plurality of sub-volumes, defining a sub-volume of the target volume as a group of a number of contiguous voxels, wherein a ratio of the number of contiguous voxels to the total number of voxels is approximately equal to the first fractional value for the sub-volume of the target volume for the target volume receiving a first violation constraint;
   for each voxel of the first plurality of sub-volumes, receiving a prescribed dose and a minimum dose constraint;
   selecting a radiation treatment plan that satisfies the first violation constraint, wherein the first violation constraint defines a fraction of the total number of voxels in the target volume that are permitted to receive a dose of radiation below the minimum dose constraint; and
   delivering radiation to the patient based on the selected radiation treatment plan.

17. The method of claim 16, wherein delivering radiation to the patient includes delivering protons, electrons, x-rays, or ions heavier than protons.

18. The method of claim 16, wherein the minimum dose constraint is a scalar value multiplied by a vector comprising elements representing the minimum prescribed dose for each voxel in the group of contiguous voxels.

19. The method of claim 16, further comprising the step of dividing the organ at risk or other non-targeted tissue into a second plurality of sub-volumes, the step comprising:
   dividing the organ at risk or other non-targeted tissue into a total number of voxels;
   selecting a second fractional value corresponding to a ratio of a size of a sub-volume of the organ at risk or other non-targeted tissue to a size of the organ at risk or other non-targeted tissue; and
   for each of the second plurality of sub-volumes, defining a sub-volume as a group of a number of contiguous voxels, wherein a ratio of the number of contiguous voxels to the total number of voxels is approximately equal to the second fractional value for the sub-volume.

20. The method of claim 19, further comprising the steps:
   for the organ at risk or other non-targeted tissue receiving a second violation constraint; and
   for each voxel of each of the second plurality of sub-volumes, receiving a maximum dose constraint.

21. The method of claim 20, wherein selecting a radiation treatment plan comprises selecting a radiation treatment plan that satisfies the second violation constraint, wherein the second violation constraint defines a fraction of the total number of voxels in the organ at risk or other non-targeted tissue that are permitted to receive a dose of radiation in excess of the maximum dose constraint.

22. The method of claim 16, wherein selecting a radiation treatment plan comprises using an inverse problem solver to determine beam characteristics predicted to deliver radiation doses to the first and/or second plurality of sub-volumes without violating at least one of the first and second violation constraints.

23. The method of claim 16, wherein determining beam characteristics comprises determining intensity.

24. An intensity-modulated radiation therapy system comprising:
   a radiation delivery system configured to deliver radiation to a patient;
   a physical processor configured to:
      analyze a representation of the patient to identify a target volume;
      divide the target volume into a total number of voxels such that the voxels can be arranged sequentially;
      define a first plurality of sub-volumes wherein a sub-volume comprises a set of a number of contiguous voxels, wherein a ratio of the number of contiguous voxels to the total number of voxels is approximately equal to a fractional value for the sub-volume;
      receive a minimum dose constraint for each voxel of the first plurality of sub-volumes;
      for the target volume, receive a first violation constraint;
      determine a radiation treatment plan that satisfies the first violation constraint; and
      select a radiation treatment plan that satisfies treatment criteria; and a control system configured to control the radiation delivery system to deliver the radiation according to the selected radiation treatment plan.

25. The system of claim 24, wherein the radiation system is configured to deliver protons.

26. The system of claim 24, wherein the radiation system is configured to deliver ions heavier than protons.

27. The system of claim 24, further comprising the steps of:
analyzing the representation of the patient to identify an organ at risk or other non-targeted tissue; and
dividing the organ at risk or other non-targeted tissue into a second plurality of sub-volumes, wherein dividing the organ at risk or other non-targeted tissue into a second plurality of sub-volumes comprises:
dividing the organ at risk or other non-targeted tissue into a total number of voxels;
selecting a second fractional value corresponding to a ratio of a size of a sub-volume of the organ at risk or other non-targeted tissue to a size of the organ at risk or other non-targeted tissue; and
for each of the second plurality of sub-volumes, defining a sub-volume as a group of a number of contiguous voxels, wherein a ratio of the number of contiguous voxels to the total number of voxels is approximately equal to the second fractional value for the sub-volume.

28. The system of claim 24, wherein the first violation constraint defines a fraction of the total number of voxels in the target volume that are permitted to receive a dose of radiation below the minimum dose constraint without violating the first violation constraint.

29. The system of claim 27, wherein the physical processor is further configured to receive a second violation constraint and a maximum dose constraint, wherein the second violation constraint defines a fraction of the total number of voxels in the organ at risk or other non-targeted tissue that are permitted to receive a dose of radiation in excess of the maximum dose constraint without violating the second violation constraint.

30. The system of claim 29, further comprising a problem solver module configured to determine radiation beam characteristics predicted to deliver radiation doses to the plurality of sub-volumes without violating one or both of the first and second violation constraints.

31. The system of claim 30, wherein the problem solving module is configured to:
determine a system of linear equations of the form $Ax^* = b$ or linear inequalities of the form $b_{min} \leq Ax^* \leq b_{max}$ where $x^*$ is a first vector comprising elements $x_i$ representing an $i^{th}$ component of a solution vector representing an actual intensity of an $i^{th}$ pencil beam, b is a second vector comprising elements $b_j$ representing a dose prescribed for a $j^{th}$ dose grid point, and A is a matrix comprising elements $a_{ij}$ representing a dose delivered by the $i^{th}$ pencil beam of unit intensity to the $j^{th}$ dose grid point;
determining one or more feasible solutions $x^*$ to the system of equations or inequalities using a feasibility-seeking algorithm; and
perturbing the one or more feasible solutions $x^*$ to determine a solution superior to a non-perturbed solution;
wherein perturbing the one or more feasible solutions comprises adding a perturbation term to the one or more feasible solutions $x^*$ that reduces total variation in dose space.

32. The system of claim 30, wherein the radiation treatment plan comprises an automatic relaxation method.

33. The system of claim 31, wherein perturbing the estimated initial solution comprises calculating a next iterate $x^{k+1}$ based on a current iterate $X^k$ using the following formula:

$$x^{k+1} = P_C(x^k + \gamma A_1^T (P_Q(A_1 x^k) - A_1 x^k)),$$

wherein $P_C(z)$ projects any vector z in intensity space orthogonally onto a set C in intensity space, $A_1$ is a matrix comprising elements $a_{ij}$ representing a dose delivered by the $i^{th}$ pencil beam of unit intensity to the $j^{th}$ dose grid point in the organ at risk, $A_1^T$ is the transpose of the matrix $A_1$, $P_Q(w)$ projects any vector w in dose space onto a set Q in dose space, $\theta$ is calculated as a squared Frobenius matrix norm of $A_1$ as follows:

$$\theta := \|A_1\|_F^2 = \sum_{i=1}^{m_1} \sum_{j=1}^{n} |a_{ij}|^2,$$

wherein $m_1$ is a total number of voxels in the organ at risk, n is a total number of pencil beams, and $\gamma$ is a parameter in the interval $0 < \gamma < 2/\theta$.

34. The method of claim 21, wherein selecting a radiation treatment plan comprises calculating a number of voxels that receive a dose of radiation in excess of the maximum dose constraint or below the minimum dose constraint.

35. The method of claim 34, wherein calculating the number of voxels that receive a dose of radiation in excess of the maximum dose constraint comprises evaluating, for any vector x, the sparsity norm $\|x\|_0 := |\{x_i \neq 0\}|$ for a vector $(Ax^* - b)$, where $|\bullet|$ denotes the cardinality of a set, where A is a matrix comprising elements $a_{ij}$ representing a dose delivered by the $i^{th}$ pencil beam of unit intensity to the $j^{th}$ dose grid point, $x^*$ is a first vector comprising elements $x_i$ representing an $i^{th}$ component of a solution vector representing an actual intensity of an $i^{th}$ pencil beam, and b is a second vector comprising elements $b_j$ representing a dose prescribed for a $j^{th}$ dose grid point.

* * * * *